(12) United States Patent
Shluzas et al.

(10) Patent No.: US 7,985,247 B2
(45) Date of Patent: Jul. 26, 2011

(54) METHODS AND APPARATUSES FOR TREATING THE SPINE THROUGH AN ACCESS DEVICE

(75) Inventors: Alan Shluzas, Millis, MA (US); James Pagliuca, Millis, MA (US); John D. Unger, Wrentham, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1329 days.

(21) Appl. No.: 10/658,736

(22) Filed: Sep. 9, 2003

(65) Prior Publication Data

US 2004/0133201 A1    Jul. 8, 2004

Related U.S. Application Data

(63) Continuation-in-part of application No. 10/280,489, filed on Oct. 25, 2002, now Pat. No. 7,056,321, and a continuation-in-part of application No. PCT/US02/28106, filed on Sep. 5, 2002.

(51) Int. Cl.
*A61B 17/88* (2006.01)

(52) U.S. Cl. ........................................... 606/281

(58) Field of Classification Search ............ 606/61, 606/99, 190, 108, 213; 600/201, 203, 204, 600/206, 210, 215, 207; 604/264
See application file for complete search history.

(56) References Cited

U.S. PATENT DOCUMENTS

| | | |
|---|---|---|
| 465,161 A | 12/1891 | Chase |
| 2,235,979 A | 3/1941 | Brown |
| 2,255,657 A | 9/1941 | Freedman |
| 2,482,116 A | 9/1949 | Lanahan |
| 2,575,253 A | 11/1951 | Bicek |
| 2,594,086 A | 4/1952 | Smith et al. |
| 2,666,428 A | 1/1954 | Glenner |
| 2,756,742 A | 7/1956 | Barton |
| 2,829,649 A | 4/1958 | Glenner |
| 2,886,004 A | 5/1959 | Morrison |
| 3,044,461 A | 7/1962 | Murdock |
| 3,486,505 A | 12/1969 | Morrison |

(Continued)

FOREIGN PATENT DOCUMENTS

AU    13672/95    9/1995

(Continued)

OTHER PUBLICATIONS

U.S. Appl. No. 11/417,616, filed May 3, 2006, Davison et al.
U.S. Appl. No. 11/417,646, filed May 3, 2006, Davison et al.
U.S. Appl. No. 11/417,653, filed May 3, 2006, Davison et al.
U.S. Appl. No. 11/417,659, filed May 3, 2006, Davison et al.
Albee, Fred H., an excerpt from "Bone Graft Surgery in Disease, Injury and Deformity", Preface (xi-x), 1940.

(Continued)

*Primary Examiner* — Nicholas Woodall
(74) *Attorney, Agent, or Firm* — Seager, Tufte & Wickhem LLC

(57) ABSTRACT

In a method of treating the spine of a patient, a fusion device is implanted via an anterior approach in an interbody space between at least two of a first vertebra, a second vertebra and a third vertebra. An access device is inserted into the patient with the access device in a first configuration having a first cross-sectional area at a distal portion thereof. The access device is actuated to a second configuration having an enlarged cross-sectional area at the distal portion thereof such that the distal portion extends across at least a portion of each of the three adjacent vertebrae. A multi-level procedure is performed through the access device across the at least three adjacent vertebrae.

10 Claims, 19 Drawing Sheets

U.S. PATENT DOCUMENTS

| | | |
|---|---|---|
| 3,570,498 A | 3/1971 | Weighton |
| 3,592,199 A | 7/1971 | Ostensen |
| 3,626,471 A | 12/1971 | Florin |
| 3,651,800 A | 3/1972 | Wilbanks |
| 3,788,318 A | 1/1974 | Kim et al. |
| 3,789,852 A | 2/1974 | Kim et al. |
| 3,875,595 A | 4/1975 | Froning |
| 3,941,127 A | 3/1976 | Froning |
| 3,964,480 A | 6/1976 | Froning |
| 4,013,078 A | 3/1977 | Feild |
| 4,049,000 A | 9/1977 | Williams |
| 4,232,660 A | 11/1980 | Coles |
| 4,254,763 A | 3/1981 | McCready et al. |
| 4,344,419 A | 8/1982 | Burgin |
| 4,350,151 A | 9/1982 | Scott |
| 4,421,108 A | 12/1983 | Cabrera et al. |
| 4,449,532 A | 5/1984 | Storz |
| 4,451,256 A | 5/1984 | Wiekl et al. |
| 4,461,281 A | 7/1984 | Carson |
| 4,498,902 A | 2/1985 | Ash et al. |
| 4,513,754 A | 4/1985 | Lee |
| 4,538,594 A | 9/1985 | Boebel et al. |
| 4,545,374 A | 10/1985 | Jacobson |
| 4,562,832 A | 1/1986 | Wilder et al. |
| 4,573,448 A | 3/1986 | Kambin |
| 4,573,454 A | 3/1986 | Hoffman |
| 4,586,491 A | 5/1986 | Carpenter |
| 4,601,713 A | 7/1986 | Fuqua |
| 4,617,929 A | 10/1986 | Gill et al. |
| 4,638,799 A | 1/1987 | Moore |
| 4,655,216 A | 4/1987 | Ticher |
| 4,674,501 A | 6/1987 | Greenberg |
| 4,678,459 A | 7/1987 | Onik et al. |
| 4,696,544 A | 9/1987 | Costella |
| 4,700,694 A | 10/1987 | Shishido |
| 4,716,901 A | 1/1988 | Jackson et al. |
| 4,736,738 A | 4/1988 | Lipovsek et al. |
| 4,750,487 A | 6/1988 | Zanetti |
| 4,762,120 A | 8/1988 | Hussein |
| 4,790,297 A * | 12/1988 | Luque ............................ 606/61 |
| 4,819,620 A | 4/1989 | Okutsu |
| 4,834,757 A | 5/1989 | Brantigan |
| 4,850,342 A | 7/1989 | Hashiguchi et al. |
| 4,862,891 A | 9/1989 | Smith et al. |
| 4,863,133 A | 9/1989 | Bonnell |
| 4,874,897 A | 10/1989 | Bickelhaupt et al. |
| 4,875,897 A | 10/1989 | Lee |
| 4,878,915 A | 11/1989 | Brantigan |
| 4,887,595 A * | 12/1989 | Heinig et al. ................... 606/61 |
| 4,899,729 A | 2/1990 | Gill et al. |
| 4,904,261 A | 2/1990 | Dove et al. |
| 4,905,082 A | 2/1990 | Nishigaki et al. |
| 4,921,478 A | 5/1990 | Solano et al. |
| 4,947,896 A | 8/1990 | Bartlett |
| 4,972,827 A | 11/1990 | Kishi et al. |
| 4,984,564 A | 1/1991 | Yuen |
| 5,004,457 A | 4/1991 | Wyatt et al. |
| 5,015,247 A | 5/1991 | Michelson |
| 5,020,514 A | 6/1991 | Heckele |
| 5,025,778 A | 6/1991 | Silverstein et al. |
| 5,071,410 A | 12/1991 | Pazekk |
| 5,108,420 A | 4/1992 | Marks |
| 5,112,354 A | 5/1992 | Sires |
| 5,125,396 A | 6/1992 | Ray |
| 5,131,382 A | 7/1992 | Meyer |
| 5,133,717 A | 7/1992 | Chopin |
| 5,139,487 A | 8/1992 | Barber |
| 5,139,499 A | 8/1992 | Small et al. |
| 5,139,511 A | 8/1992 | Gill et al. |
| 5,158,543 A | 10/1992 | Lazarus |
| 5,163,949 A | 11/1992 | Bonutti |
| 5,171,279 A | 12/1992 | Mathews |
| 5,190,561 A | 3/1993 | Graber |
| 5,195,507 A | 3/1993 | Bilweis |
| 5,195,541 A | 3/1993 | Obenchain |
| 5,197,971 A | 3/1993 | Bonutti |
| 5,201,729 A | 4/1993 | Hertzmann et al. |
| 5,224,680 A | 7/1993 | Greenstein et al. |
| 5,225,001 A | 7/1993 | Manni et al. |
| 5,242,444 A | 9/1993 | MacMillan |
| 5,279,564 A | 1/1994 | Taylor et al. |
| 5,287,845 A | 2/1994 | Faul et al. |
| 5,295,994 A | 3/1994 | Bonutti |
| 5,312,417 A | 5/1994 | Wilk |
| 5,313,962 A | 5/1994 | Obenchain |
| 5,330,473 A | 7/1994 | Howland |
| 5,334,150 A | 8/1994 | Kaali |
| 5,339,802 A | 8/1994 | Cook |
| 5,339,803 A | 8/1994 | Mayzels et al. |
| 5,345,927 A | 9/1994 | Bonutti |
| 5,346,504 A | 9/1994 | Ortiz et al. |
| 5,353,784 A | 10/1994 | Nady-Mohamed |
| 5,354,302 A | 10/1994 | Ko |
| 5,357,983 A | 10/1994 | Mathews |
| 5,359,995 A | 11/1994 | Sewell, Jr. |
| 5,360,431 A | 11/1994 | Puno et al. |
| 5,364,395 A | 11/1994 | West, Jr. |
| 5,370,647 A | 12/1994 | Graber et al. |
| 5,376,076 A | 12/1994 | Kaali |
| 5,380,291 A | 1/1995 | Kaali |
| 5,385,583 A | 1/1995 | Cotrel |
| 5,392,766 A | 2/1995 | Masterson et al. |
| 5,395,317 A | 3/1995 | Kambin |
| 5,396,880 A | 3/1995 | Kagan et al. |
| 5,437,637 A | 8/1995 | Lieber et al. |
| 5,437,671 A | 8/1995 | Lozier et al. |
| 5,437,672 A | 8/1995 | Alleyne |
| 5,439,449 A | 8/1995 | Mapes et al. |
| 5,439,464 A | 8/1995 | Shapiro |
| 5,441,041 A | 8/1995 | Sauer et al. |
| 5,441,042 A | 8/1995 | Putman |
| 5,443,058 A | 8/1995 | Ough |
| 5,443,467 A | 8/1995 | Biedermann et al. |
| 5,443,514 A | 8/1995 | Steffee |
| 5,445,142 A | 8/1995 | Hassler, Jr. |
| 5,454,365 A | 10/1995 | Bonutti |
| 5,470,333 A | 11/1995 | Ray |
| 5,472,426 A | 12/1995 | Bonati et al. |
| 5,480,440 A | 1/1996 | Kambin |
| 5,484,437 A | 1/1996 | Michelson |
| 5,487,744 A | 1/1996 | Howland |
| 5,489,307 A | 2/1996 | Kuslich et al. |
| 5,503,617 A | 4/1996 | Jako |
| 5,512,034 A | 4/1996 | Finn et al. |
| 5,520,607 A | 5/1996 | Frassica et al. |
| 5,534,009 A | 7/1996 | Lander |
| 5,549,595 A | 8/1996 | Freitas |
| 5,549,608 A | 8/1996 | Errico et al. |
| 5,551,947 A | 9/1996 | Kaali |
| 5,554,157 A | 9/1996 | Errico et al. |
| 5,556,371 A | 9/1996 | Schulken et al. |
| 5,562,696 A | 10/1996 | Nobles et al. |
| 5,562,736 A | 10/1996 | Dickhudt et al. |
| 5,569,205 A | 10/1996 | Hart et al. |
| 5,569,248 A | 10/1996 | Mathews |
| 5,571,072 A | 11/1996 | Kronner |
| 5,573,517 A | 11/1996 | Bonutti et al. |
| 5,575,754 A | 11/1996 | Konomura |
| 5,586,984 A | 12/1996 | Errico et al. |
| 5,588,949 A | 12/1996 | Taylor et al. |
| 5,601,554 A | 2/1997 | Howland et al. |
| 5,601,590 A | 2/1997 | Bonutti et al. |
| 5,601,690 A | 2/1997 | Gauld et al. |
| 5,603,688 A | 2/1997 | Upsher |
| 5,603,713 A * | 2/1997 | Aust et al. ..................... 606/61 |
| 5,613,937 A | 3/1997 | Garrison et al. |
| 5,613,968 A | 3/1997 | Lin |
| 5,624,442 A | 4/1997 | Mellinger et al. |
| 5,642,442 A | 6/1997 | Merllinger et al. |
| 5,643,282 A | 7/1997 | Kieturakis |
| 5,667,472 A | 9/1997 | Finn et al. |
| 5,667,473 A | 9/1997 | Finn et al. |
| 5,667,478 A | 9/1997 | McFarlin et al. |
| 5,667,520 A | 9/1997 | Bonutti |
| 5,672,176 A | 9/1997 | Biedermann et al. |
| 5,674,295 A | 10/1997 | Ray et al. |
| 5,681,319 A | 10/1997 | Biedermann et al. |

| Patent | Kind | Date | Inventor | Ref |
|---|---|---|---|---|
| 5,683,391 A * | | 11/1997 | Boyd | 606/61 |
| 5,695,448 A | | 12/1997 | Kimura et al. | |
| 5,702,454 A | | 12/1997 | Baumgartner | |
| 5,707,359 A | | 1/1998 | Bufalini | |
| 5,716,356 A | | 2/1998 | Biedermann et al. | |
| 5,725,588 A | | 3/1998 | Errico et al. | |
| 5,728,046 A | | 3/1998 | Mayer et al. | |
| 5,730,754 A | | 3/1998 | Obenchain | |
| 5,735,792 A | | 4/1998 | Vanden Hoek et al. | |
| 5,762,629 A | | 6/1998 | Kambin | |
| 5,772,661 A | | 6/1998 | Michelson | |
| 5,782,833 A | | 7/1998 | Haider | |
| 5,782,919 A | | 7/1998 | Zdeblick et al. | |
| 5,792,044 A * | | 8/1998 | Foley et al. | 600/114 |
| 5,795,289 A | | 8/1998 | Wyttenbach | |
| 5,797,911 A | | 8/1998 | Sherman et al. | |
| 5,810,809 A | | 9/1998 | Rydell | |
| 5,810,818 A | | 9/1998 | Errico et al. | |
| 5,813,978 A | | 9/1998 | Jako | |
| 5,814,084 A | | 9/1998 | Grivas et al. | |
| 5,823,947 A | | 10/1998 | Yoon et al. | |
| 5,824,093 A | | 10/1998 | Ray et al. | |
| 5,827,319 A | | 10/1998 | Carlson et al. | |
| 5,857,999 A | | 1/1999 | Quick et al. | |
| 5,863,293 A | | 1/1999 | Richelsoph | |
| 5,865,728 A | | 2/1999 | Moll et al. | |
| 5,865,802 A | | 2/1999 | Yoon et al. | |
| 5,868,745 A | | 2/1999 | Alleyne | |
| 5,873,878 A | | 2/1999 | Harms et al. | |
| 5,876,402 A | | 3/1999 | Errico et al. | |
| 5,879,389 A | | 3/1999 | Koshino | |
| 5,882,350 A | | 3/1999 | Ralph et al. | |
| 5,885,286 A | | 3/1999 | Sherman et al. | |
| 5,888,190 A | | 3/1999 | Meyer et al. | |
| 5,902,231 A | | 5/1999 | Foley et al. | |
| 5,910,142 A | | 6/1999 | Tatar | |
| 5,921,917 A | | 7/1999 | Barthel et al. | |
| 5,928,137 A | | 7/1999 | Green | |
| 5,928,232 A | | 7/1999 | Howland et al. | |
| 5,928,233 A | | 7/1999 | Apfelbaum et al. | |
| 5,954,635 A | | 9/1999 | Foley et al. | |
| 5,954,725 A | | 9/1999 | Sherman et al. | |
| 5,961,499 A | | 10/1999 | Bonutti et al. | |
| 5,961,517 A | | 10/1999 | Biedermann et al. | |
| 5,964,760 A | | 10/1999 | Richelsoph | |
| 5,984,928 A | | 11/1999 | Hermann | |
| 5,997,471 A | | 12/1999 | Gumb et al. | |
| 5,997,508 A | | 12/1999 | Lunn et al. | |
| 6,004,320 A | | 12/1999 | Casscells et al. | |
| 6,007,487 A | | 12/1999 | Foley et al. | |
| 6,007,533 A | | 12/1999 | Casscells et al. | |
| 6,010,503 A | | 1/2000 | Richelsoph et al. | |
| 6,022,376 A | | 2/2000 | Assell et al. | |
| 6,033,406 A * | | 3/2000 | Mathews | 606/61 |
| 6,050,997 A | | 4/2000 | Mullane | |
| 6,053,917 A | | 4/2000 | Sherman et al. | |
| 6,063,090 A | | 5/2000 | Schläpfer | |
| 6,074,380 A | | 6/2000 | Byrne et al. | |
| 6,074,391 A | | 6/2000 | Metz-Stavenhagen et al. | |
| 6,077,262 A | | 6/2000 | Schläpfer et al. | |
| 6,086,588 A | | 7/2000 | Ameil et al. | |
| 6,090,111 A | | 7/2000 | Nichols | |
| 6,096,081 A | | 8/2000 | Grivas et al. | |
| 6,110,173 A | | 8/2000 | Thomas, Jr. | |
| 6,110,210 A | | 8/2000 | Norton et al. | |
| 6,113,601 A | | 9/2000 | Tatar | |
| 6,120,434 A | | 9/2000 | Kimura et al. | |
| 6,120,437 A | | 9/2000 | Yoon et al. | |
| 6,132,432 A | | 10/2000 | Richelsoph | |
| 6,132,465 A | | 10/2000 | Ray et al. | |
| 6,139,550 A | | 10/2000 | Michelson | |
| 6,142,931 A | | 11/2000 | Kaji | |
| 6,152,871 A | | 11/2000 | Foley et al. | |
| 6,162,170 A | | 12/2000 | Foley et al. | |
| 6,162,236 A | | 12/2000 | Osada | |
| 6,171,299 B1 | | 1/2001 | Bonutti | |
| 6,175,758 B1 | | 1/2001 | Kambin | |
| 6,176,823 B1 | | 1/2001 | Foley et al. | |
| 6,183,473 B1 | | 2/2001 | Ashman | |
| 6,187,000 B1 | | 2/2001 | Davison et al. | |
| 6,193,715 B1 | | 2/2001 | Wrublewski et al. | |
| 6,206,822 B1 | | 3/2001 | Foley et al. | |
| 6,214,001 B1 | | 4/2001 | Casscells et al. | |
| 6,217,509 B1 | | 4/2001 | Foley et al. | |
| 6,221,082 B1 | | 4/2001 | Marino et al. | |
| 6,248,105 B1 | | 6/2001 | Schläpfer et al. | |
| 6,258,024 B1 | | 7/2001 | van Der Weegen | |
| 6,261,586 B1 | | 7/2001 | McCay | |
| 6,267,765 B1 | | 7/2001 | Taylor et al. | |
| 6,270,498 B1 | | 8/2001 | Michelson | |
| 6,280,442 B1 | | 8/2001 | Barker et al. | |
| 6,293,949 B1 * | | 9/2001 | Justis et al. | 606/61 |
| 6,296,642 B1 | | 10/2001 | Morrison et al. | |
| 6,306,137 B2 | | 10/2001 | Troxell | |
| 6,306,170 B2 | | 10/2001 | Ray | |
| 6,309,391 B1 | | 10/2001 | Crandall et al. | |
| 6,312,443 B1 | | 11/2001 | Stone | |
| 6,325,812 B1 | | 12/2001 | Dubrul et al. | |
| 6,338,730 B1 | | 1/2002 | Bonutti et al. | |
| 6,355,038 B1 | | 3/2002 | Pisharodi | |
| 6,355,040 B1 | | 3/2002 | Richelsoph et al. | |
| 6,358,226 B1 | | 3/2002 | Ryan | |
| 6,358,266 B1 | | 3/2002 | Bonutti | |
| 6,361,488 B1 | | 3/2002 | Davison et al. | |
| 6,368,321 B1 | | 4/2002 | Jackson | |
| 6,371,968 B1 | | 4/2002 | Kogasaka et al. | |
| 6,383,195 B1 | | 5/2002 | Richard | |
| 6,387,130 B1 | | 5/2002 | Stone et al. | |
| 6,425,859 B1 | | 7/2002 | Foley et al. | |
| 6,440,133 B1 | | 8/2002 | Beale et al. | |
| 6,440,137 B1 | | 8/2002 | Horvath et al. | |
| 6,471,703 B1 | | 10/2002 | Ashman | |
| 6,478,797 B1 | | 11/2002 | Paul | |
| 6,482,207 B1 | | 11/2002 | Errico | |
| 6,485,491 B1 | | 11/2002 | Farris et al. | |
| 6,485,494 B1 | | 11/2002 | Haider | |
| 6,485,518 B1 | | 11/2002 | Cornwall et al. | |
| 6,494,893 B2 | | 12/2002 | Dubrul et al. | |
| 6,497,654 B1 | | 12/2002 | Leonard et al. | |
| 6,503,249 B1 | | 1/2003 | Krause | |
| 6,508,839 B1 | | 1/2003 | Lambrecht et al. | |
| 6,520,907 B1 | | 2/2003 | Foley et al. | |
| 6,524,320 B2 | | 2/2003 | DiPoto | |
| 6,530,880 B2 | | 3/2003 | Pagliuca | |
| 6,530,926 B1 | | 3/2003 | Davison | |
| 6,530,929 B1 | | 3/2003 | Justis et al. | |
| 6,530,930 B1 | | 3/2003 | Marino et al. | |
| 6,540,748 B2 | | 4/2003 | Lombardo | |
| 6,564,078 B1 | | 5/2003 | Marino et al. | |
| 6,575,899 B1 | | 6/2003 | Foley et al. | |
| 6,602,291 B1 | | 8/2003 | Ray et al. | |
| 6,610,094 B2 | | 8/2003 | Husson | |
| 6,648,888 B1 | | 11/2003 | Shluzas | |
| 6,652,553 B2 | | 11/2003 | Davison et al. | |
| 6,679,833 B2 | | 1/2004 | Smith et al. | |
| 6,793,656 B1 * | | 9/2004 | Mathews | 606/61 |
| 6,800,084 B2 | | 10/2004 | Davison et al. | |
| 6,811,558 B2 | | 11/2004 | Davison et al. | |
| 6,821,243 B2 | | 11/2004 | Pagliuca et al. | |
| 6,837,889 B2 | | 1/2005 | Shluzas | |
| 6,837,891 B2 | | 1/2005 | Davison et al. | |
| 7,001,397 B2 | | 2/2006 | Davison | |
| 7,033,369 B2 | | 4/2006 | Davison et al. | |
| 7,056,321 B2 | | 6/2006 | Pagliuca et al. | |
| 7,108,705 B2 | | 9/2006 | Davison et al. | |
| 2001/0001119 A1 | | 5/2001 | Lombardo | |
| 2001/0011170 A1 | | 8/2001 | Davison et al. | |
| 2001/0049498 A1 | | 12/2001 | Davison et al. | |
| 2002/0002360 A1 | | 1/2002 | Orth et al. | |
| 2002/0010467 A1 | | 1/2002 | Cooper et al. | |
| 2002/0022764 A1 | | 2/2002 | Smith et al. | |
| 2002/0026193 A1 | | 2/2002 | Barker et al. | |
| 2002/0065560 A1 | | 5/2002 | Varga et al. | |
| 2002/0143235 A1 | | 10/2002 | Pagliuca | |
| 2002/0161368 A1 | | 10/2002 | Foley et al. | |
| 2002/0165612 A1 | | 11/2002 | Gerber et al. | |
| 2003/0009130 A1 | | 1/2003 | Stecker et al. | |
| 2003/0014068 A1 | | 1/2003 | Bonutti et al. | |

| | | | |
|---|---|---|---|
| 2003/0040656 A1 | 2/2003 | Pagliuca et al. | |
| 2003/0073998 A1 | 4/2003 | Pagliuca et al. | |
| 2003/0139648 A1 | 7/2003 | Foley et al. | |
| 2003/0153911 A1 | 8/2003 | Shluzas | |
| 2003/0153927 A1 | 8/2003 | DiPoto et al. | |
| 2003/0167058 A1 | 9/2003 | Shluzas | |
| 2003/0191371 A1 | 10/2003 | Smith et al. | |
| 2003/0195405 A1 | 10/2003 | Marino et al. | |
| 2003/0195493 A1 | 10/2003 | Davison et al. | |
| 2003/0195549 A1 | 10/2003 | Davison et al. | |
| 2003/0195550 A1 | 10/2003 | Davison et al. | |
| 2003/0195551 A1 | 10/2003 | Davison et al. | |
| 2003/0199871 A1 | 10/2003 | Foley et al. | |
| 2003/0199885 A1 | 10/2003 | Davison et al. | |
| 2003/0208203 A1 | 11/2003 | Lim et al. | |
| 2003/0236529 A1 | 12/2003 | Shluzas et al. | |
| 2004/0059339 A1 | 3/2004 | Roehm, III et al. | |
| 2004/0078051 A1 | 4/2004 | Davison et al. | |
| 2004/0098012 A1 | 5/2004 | Davison et al. | |
| 2004/0116954 A1 | 6/2004 | Davison et al. | |
| 2004/0133201 A1 | 7/2004 | Shluzas et al. | |
| 2004/0176763 A1 | 9/2004 | Foley et al. | |
| 2004/0236317 A1 | 11/2004 | Davison | |
| 2005/0021030 A1 | 1/2005 | Pagliuca et al. | |
| 2005/0033297 A1 | 2/2005 | Davison | |
| 2005/0043754 A1 | 2/2005 | Davison et al. | |
| 2005/0113833 A1 | 5/2005 | Davison | |
| 2006/0089662 A1 | 4/2006 | Davison et al. | |

FOREIGN PATENT DOCUMENTS

| | | | |
|---|---|---|---|
| DE | 1566116 | | 1/1970 |
| DE | 2222979 | | 11/1973 |
| DE | 3108766 | A1 | 9/1982 |
| DE | 3936811 | A1 | 9/1990 |
| EP | 0 303 824 | A2 | 2/1989 |
| EP | 0 528 562 | A2 | 7/1992 |
| EP | 0 682 918 | A1 | 11/1995 |
| EP | 0 807 415 | A2 | 11/1997 |
| EP | 0 980 677 | A1 | 2/2000 |
| EP | 1 090 595 | A2 | 4/2001 |
| EP | 1 251 767 | A2 | 10/2002 |
| EP | 1 305 077 | A1 | 5/2003 |
| FR | 2 701 379 | | 8/1994 |
| FR | 2 714 285 | A1 | 6/1995 |
| GB | 2234906 | A | 2/1991 |
| JP | 2000-83960 | A2 | 3/2000 |
| JP | 2001-149376 | A2 | 6/2001 |
| WO | WO 8303189 | A * | 9/1983 |
| WO | WO 91/06266 | A1 | 5/1991 |
| WO | WO 92/19146 | A1 | 11/1992 |
| WO | WO 92/21292 | A2 | 12/1992 |
| WO | WO 93/14801 | A1 | 8/1993 |
| WO | WO 93/15647 | A1 | 8/1993 |
| WO | WO 94/03114 | A1 | 2/1994 |
| WO | WO 95/10218 | A1 | 4/1995 |
| WO | WO 95/22285 | A1 | 8/1995 |
| WO | WO 95/32663 | A1 | 12/1995 |
| WO | WO 98/27884 | A1 | 7/1998 |
| WO | WO 98/33462 | A1 | 8/1998 |
| WO | WO 00/18306 | A1 | 4/2000 |
| WO | WO 01/54560 | A2 | 8/2001 |
| WO | WO 02/09801 | A1 | 2/2002 |
| WO | WO 02/22030 | A2 | 3/2002 |
| WO | WO 02/078767 | A2 | 10/2002 |
| WO | WO 03/007783 | A2 | 1/2003 |
| WO | 2004021899 | | 3/2004 |

OTHER PUBLICATIONS

Caspar, Wolfhard, M.D., "The Caspar Microsurgical Discetomy and Comparison with a Conventional Standard Lumbar Disc Procedure" Neurosurgery, Jan. 1991, pp. 78-87, vol. 28, No. 1.

Destandau, Jean, "A Special Device for Endoscopic Surgery of Lumbar Disc Herniation", Neurological Research, Jan. 1999, vol. 21, pp. 39-42.

Ditsworth, David A., M.D., The American Association of Neurological Surgeons, Apr. 1995, "Comprehensive Percutaneous Endoscopic Spinal Surgery", Abstract.

Ditsworth, David A., M.D., The Joint Section on Spine and Peripheral Nerves, Feb. 1995, "A New and Superior Technique for Removal of Herniated Lumbar Disc: Endoscope and Nucleotome Combination", Abstract.

Ditsworth, David A., M.D., "Endoscopic Transforaminal Lumbar Discectomy and Reconfiguration: A Posterolateral Approach into the Spinal Canal", Surg Neurol, 1998; 49-588-98.

Endius presentation materials (2 pgs.) entitled "Spine Endoscopy System with FlexPosure™", dated 1999.

Foley, Kevin T., M.D., et al., "Percutaneous Pedicle Screw Fixation of the Lumbar Spine", Neurosurg Focus, 10:1-8, Apr. 2001.

Guiot, Bernard H., M.S., et al., "A Minimally Invasive Technique for Decompression of the Lumbar Spine", SPINE, 27, 4:432-438, 2002.

Kambin, Parviz, "Arthroscopic Lumbar Interbody Fusion", Publisher Unknown, Chapter 77:1055-1066, undated.

Kambin, Parviz, "Posterolateral Percutaneous Lumbar Interbody Fusion", Publisher Unknown, Chapter 9:117-121, Date Unknown.

Kambin, Parviz, *Advances in Operative Orthopaedics*, 3:147-171, 1995, "The Role of Minimally Invasive Spine Surgery".

Kambin, Parviz, *Neurosurgery Clinics of North America*, 7(1):65-76, 1996 "Diagnostic and Therapeutic Spinal Arthroscopy".

Kambin, Parviz, "Arthroscopic Techniques for Spinal Surgery", Chapter 89, Operative Arthroscopy, Second Edition, pp. 1215-1225, 1996.

Kambin, Parviz, "Arthroscopic Microdiscectomy", The Adult Spine, Principles and Practice, Chapter 94, pp. 2023-2036, 1997.

Kambin, Parviz, "Arthroscopic Lumbar Intervertebral Fusion", The Adult Spine: Principles and Practice, Chapter 95, pp. 2037-2046, 1997.

Kambin, Parviz M.D., Endoscopic Laminotomy Procedures, on sale and in public use in the United States more than one year prior to Aug. 1, 2000.

Leonard Medical, Inc., Brochure entitled "Instruments for Less Invasive Surgery," undated, published more than one year prior to Aug. 1, 2000.

Mathews, Hallet H., M.D., "Spinal Endoscopy Evolution, Applications, and Foundations," pp. 1-44.

MED™ presentation materials (33 pgs.) entitled "MicroEndoscopic Discectomy System", dated 1997.

Medtronic SOFAMOR DANEK METRx Micro Discectomy System Brochure, 2000.

Medtronic SOFAMOR DANEK, An Evolution in Minimally Invasive Spine Surgery, METRx MicroEndoscopic Discectomy, 1999.

Medtronic SOFAMOR DANEK, METRx Microdiscectomy Surgical Technique, 2001 as described by Donald L. Hilton, Jr., M.D., F.A.C.S. and Sylvain Palmer, M.D., F.A.C.S.

Musculoskeletal Transplant Foundation presentation materials (2 pgs.) entitled "The MTF EndoDowel™", dated Jun. 1996.

Musculoskeletal Transplant Foundation presentation materials (1-16), dated Apr. 1996.

Otero Vich M.D., Jose M., "Anterior Cervical Interbody Fusion with Threaded Cylindrical Bone", Journal of Neurosurgery 63: 750-753, 1985.

SOFAMOR DANEK, Micro Endo Systems Brochure, 1994.

SOFAMOR DANEK, Laparoscopic Bone Dowel Instruments Brochure, 1995.

SOFAMOR DANEK, Laparoscopic Bone Dowel Surgical Technique, (17 pgs.) 1995.

Stauber, Martin H., M.D. et al., "Pedicle Screw Placement with Intraosseous Endoscopy", SPINE, 19, 1:57-61, 1994.

U.S. Appl. No. 07/328,952, Material cancelled from Meyer Application. Mailed Mar. 27, 1989, publicly available at least on Jul. 21, 1992.

Request for Declaration of Interference filed in U.S. Appl. No. 10/734,161, filed Jan. 29, 2004.

Response to Office Action dated Jan. 3, 2006 in U.S. Appl. No. 10/734,161, filed Jul. 3, 2006.

Letter and Suggestion of Interference in U.S. Appl. No. 10/734,161, filed Oct. 25, 2006.

* cited by examiner

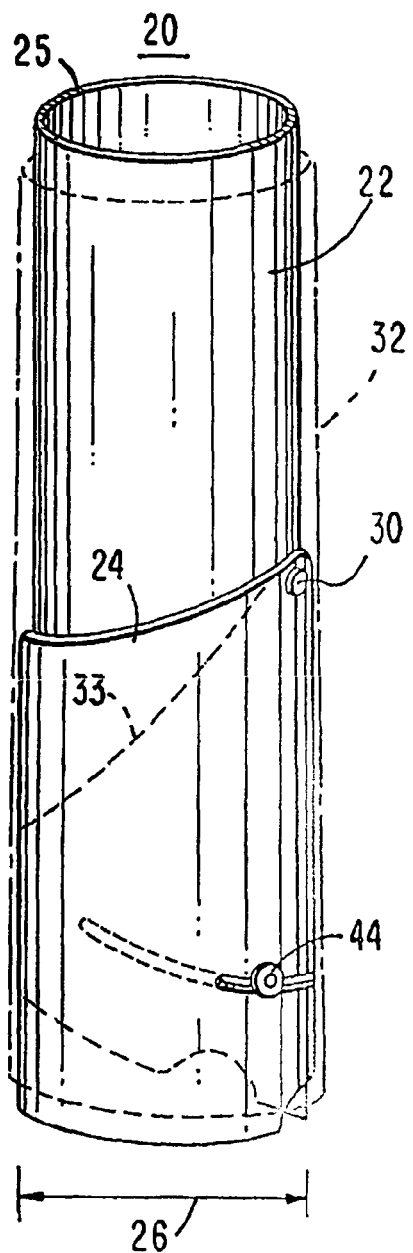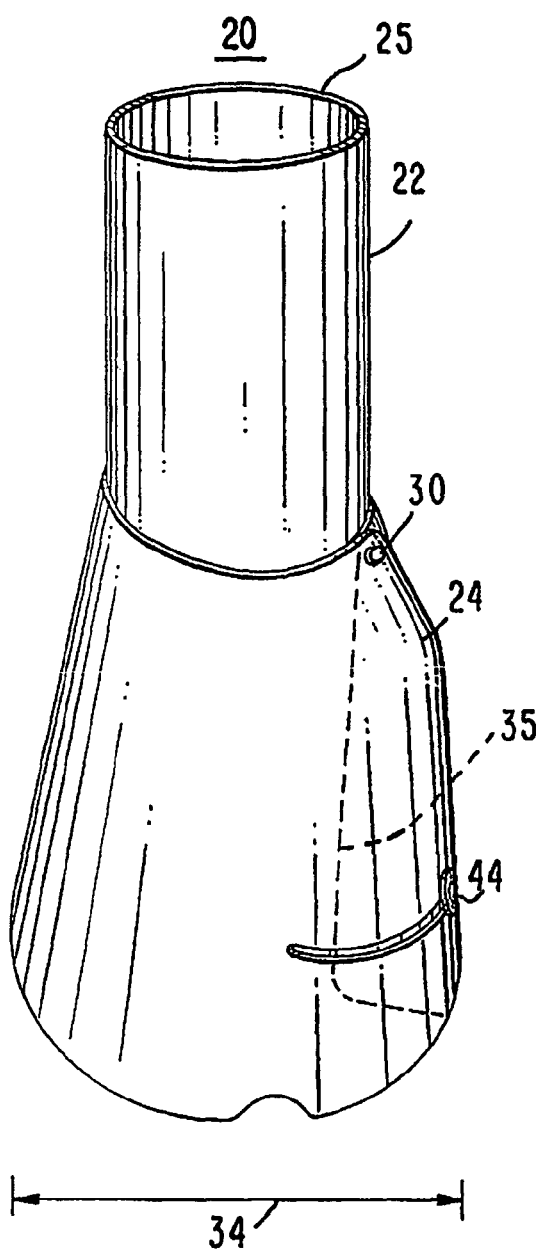

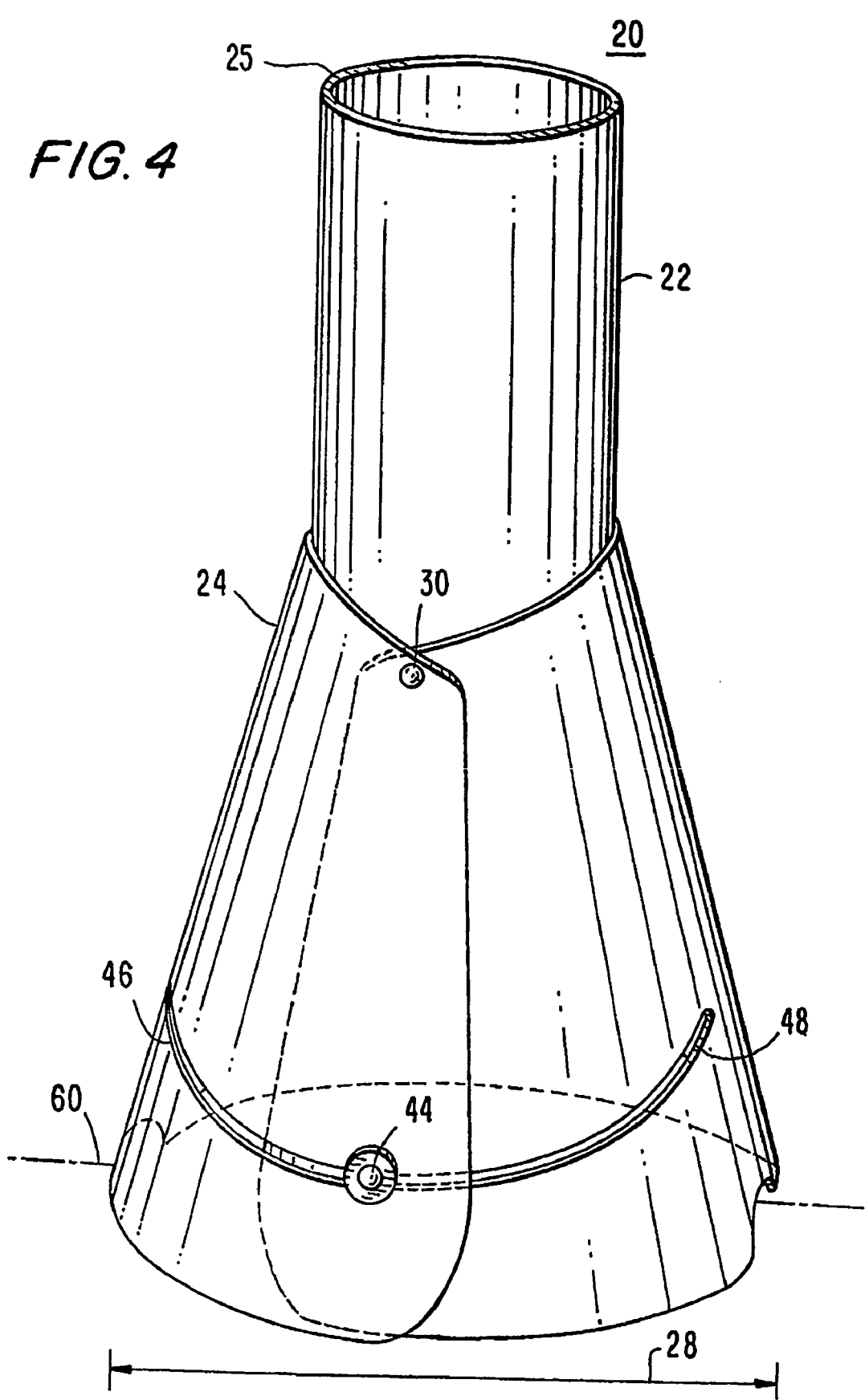

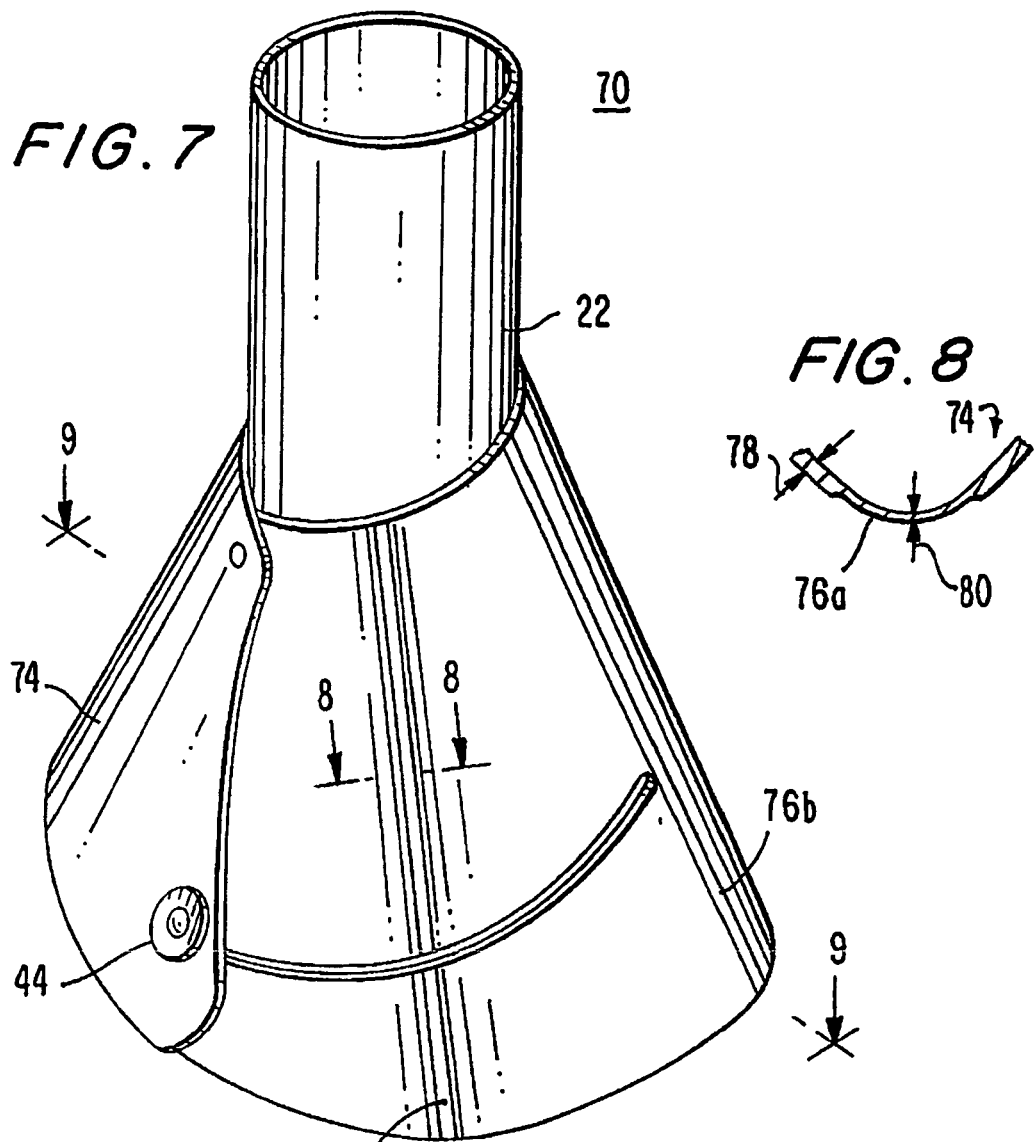

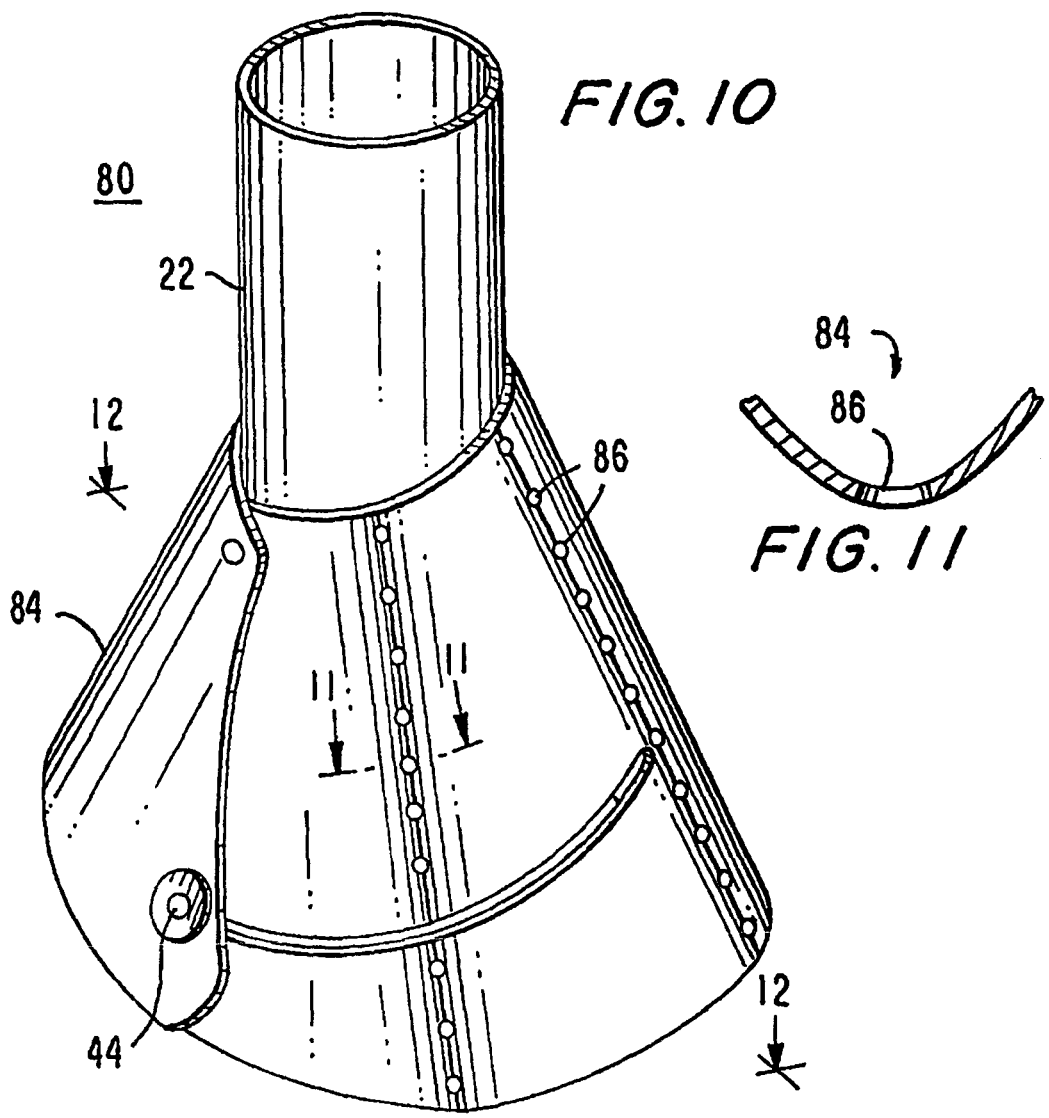
FIG. 10
FIG. 11
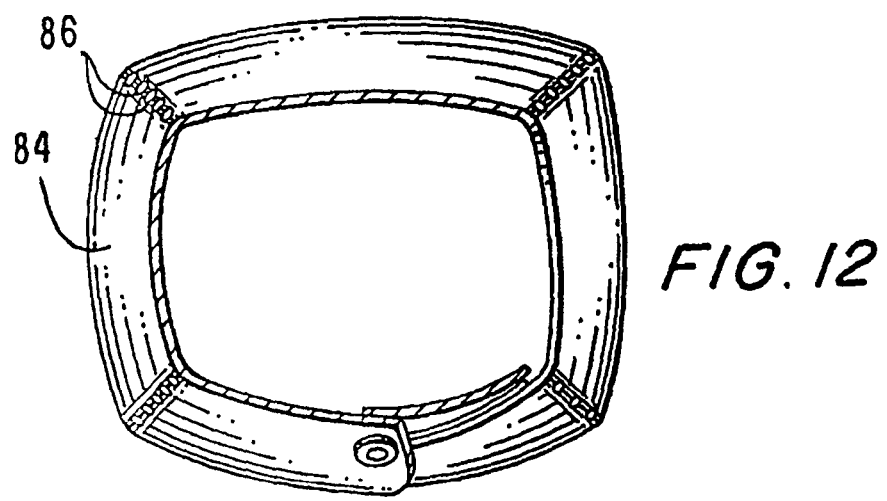
FIG. 12

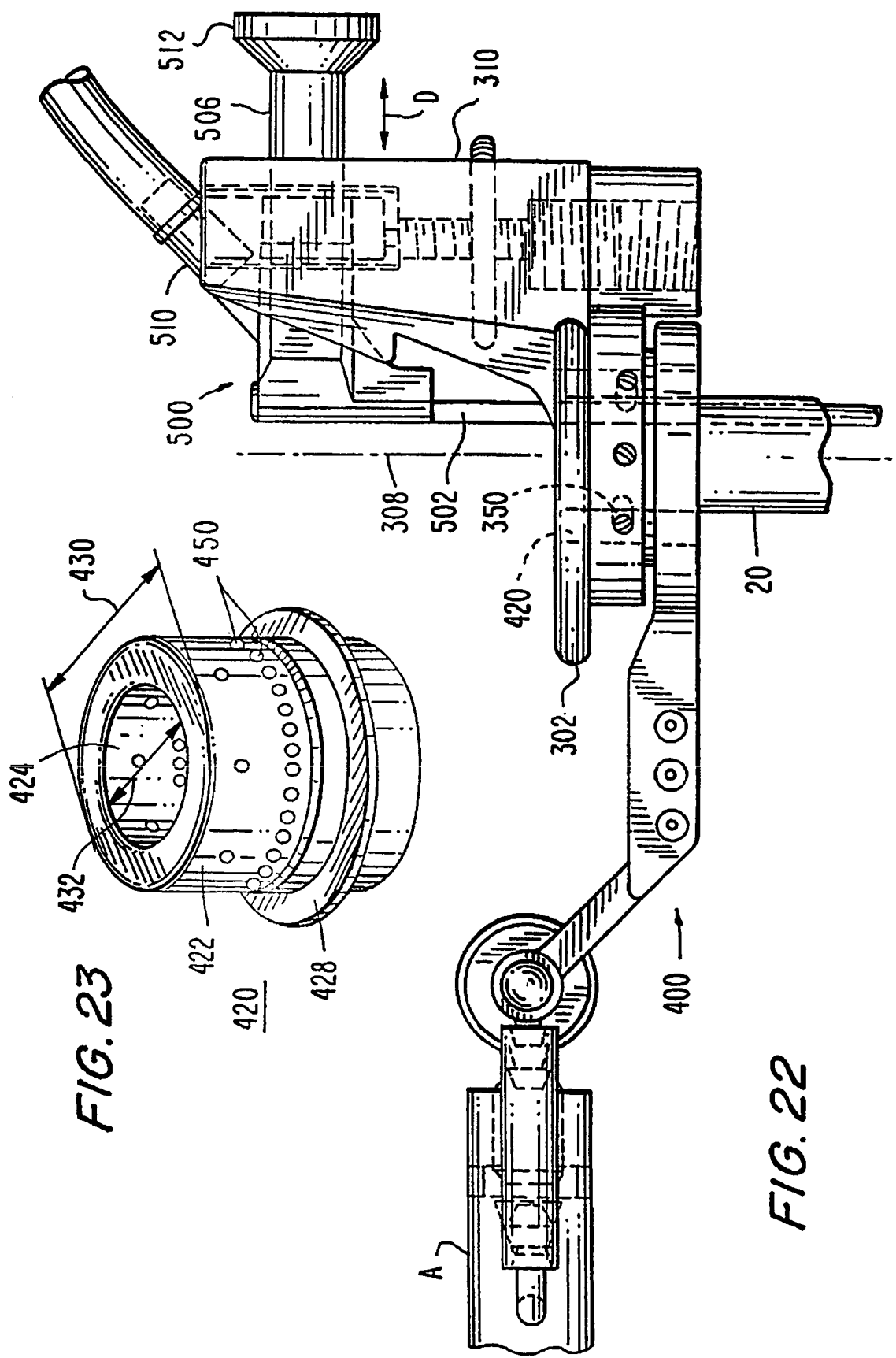

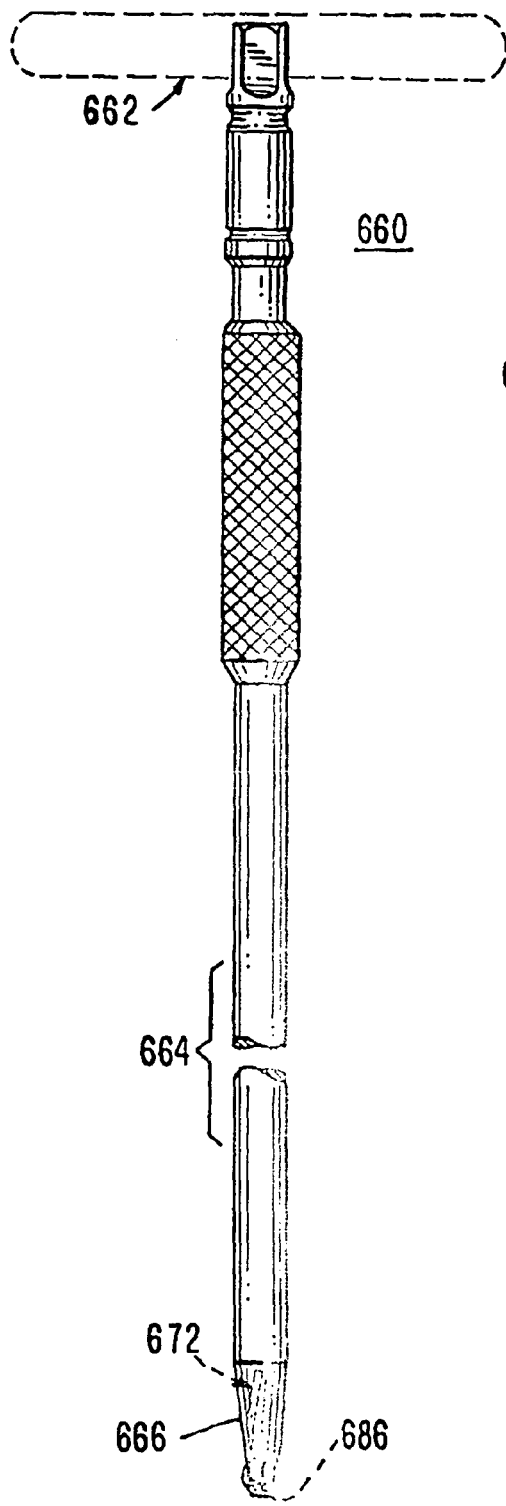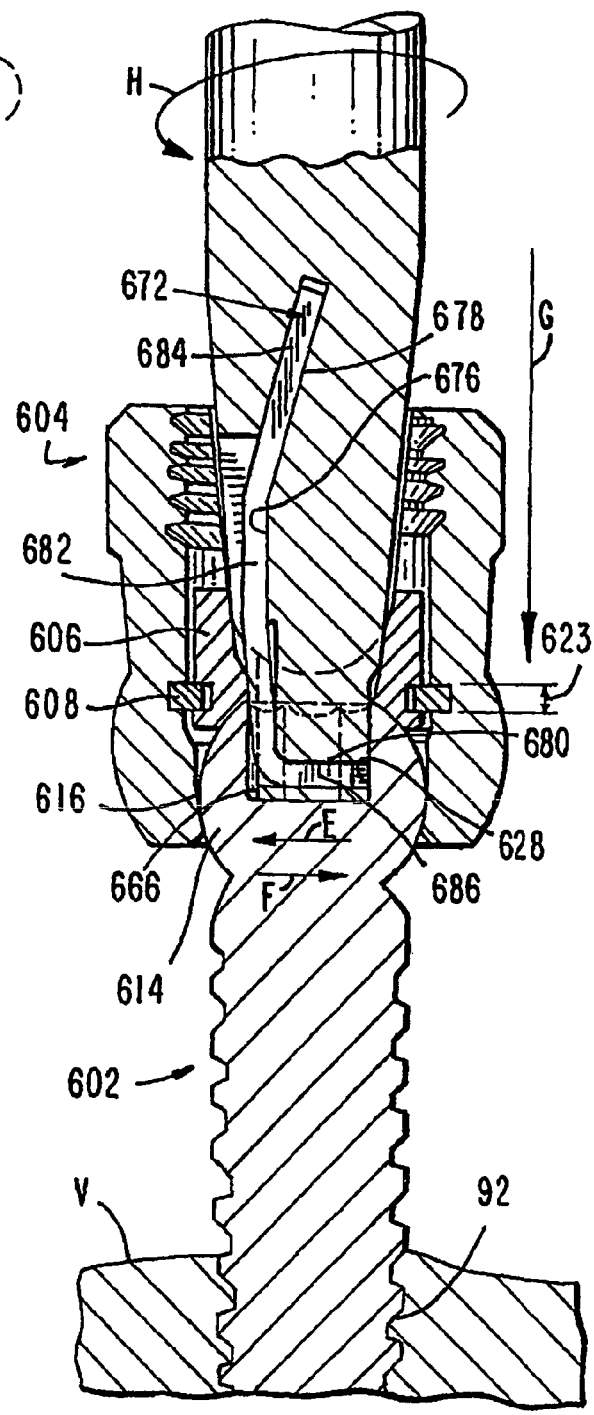

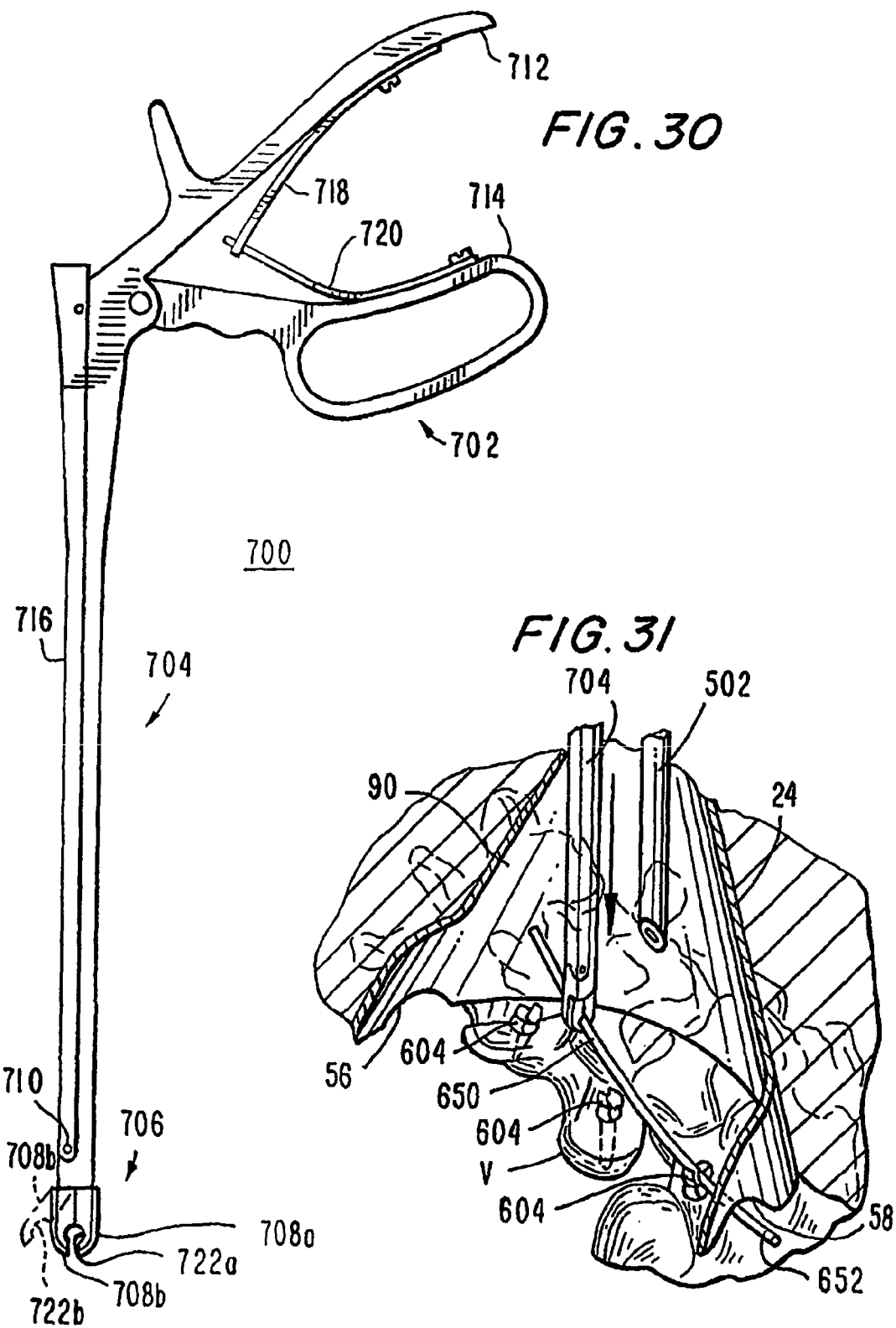

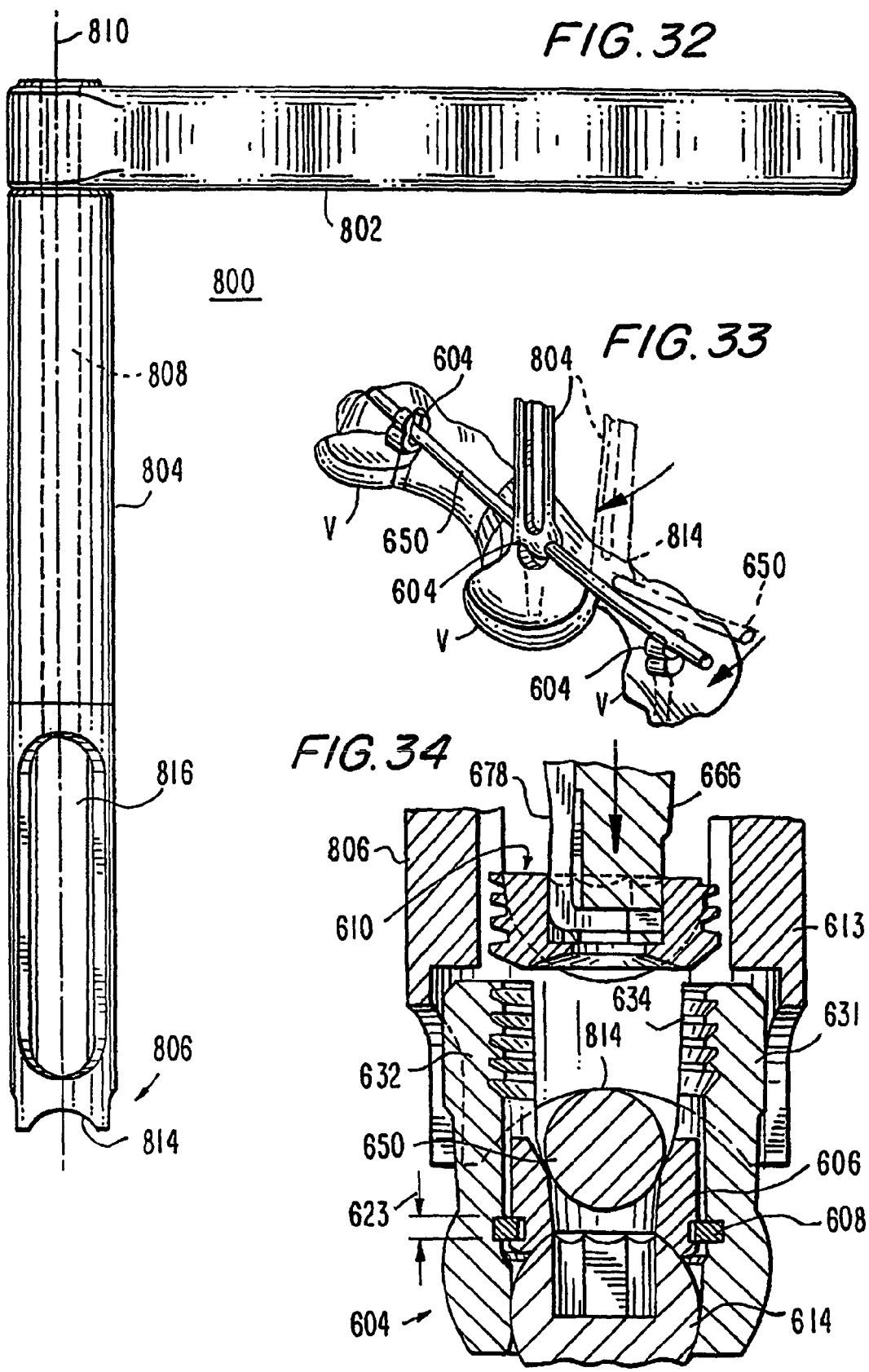

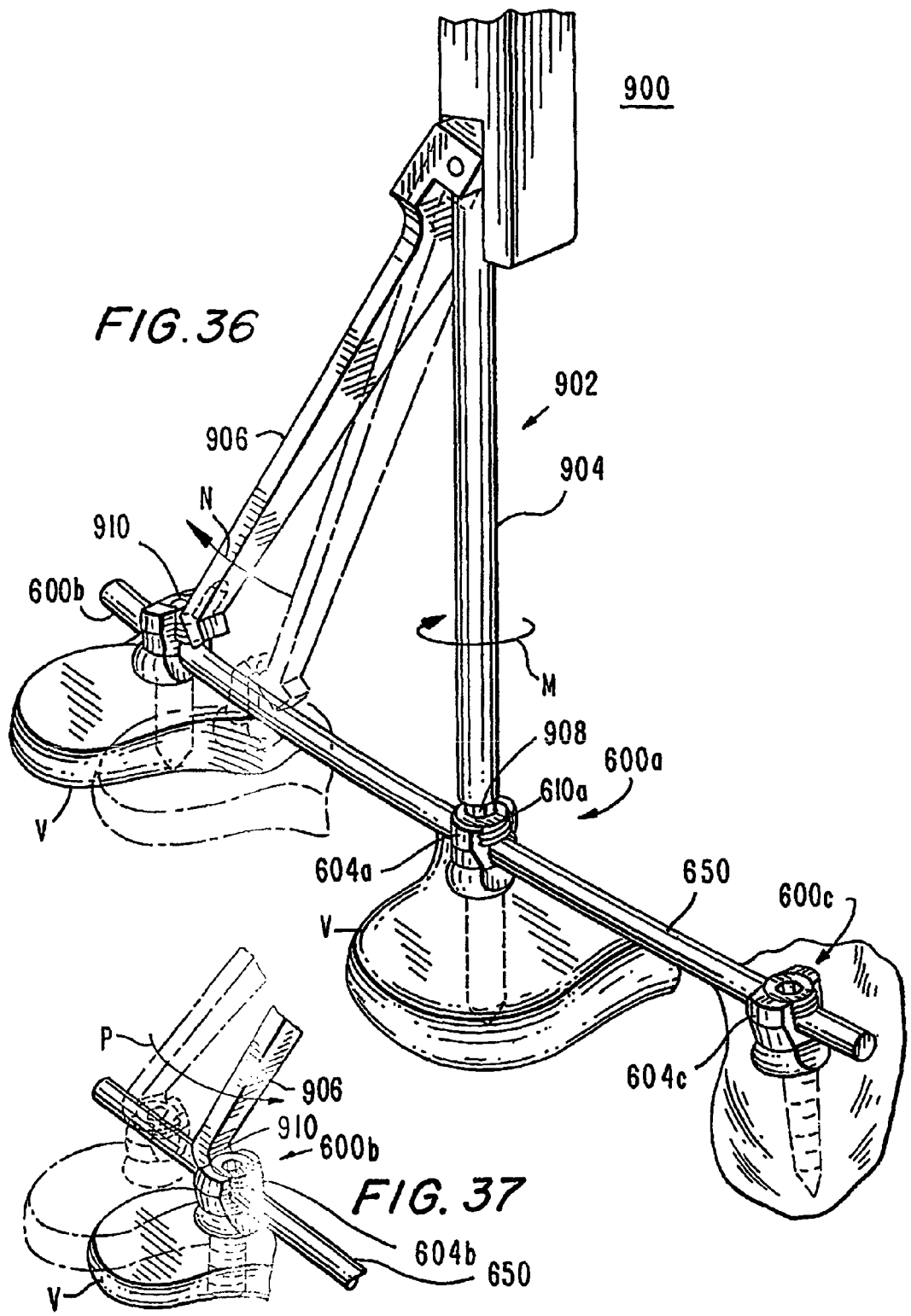

METHODS AND APPARATUSES FOR TREATING THE SPINE THROUGH AN ACCESS DEVICE

RELATED APPLICATIONS

This application is a continuation-in-part of International Application PCT/US02/28106, with an international filing date of Sep. 5, 2002, to be published in English under PCT article 21(2), and is a continuation-in-part of U.S. application Ser. No. 10/280,489, with a filing date of Oct. 25, 2002 now U.S. Pat. No. 7,056,321, which is incorporated by reference hereinbelow in its entirety.

BACKGROUND OF THE INVENTION

1. Field of the Invention

This invention relates to methods and apparatuses for performing minimally invasive surgery, and more particularly to instruments for providing access to body tissues and performing procedures on bone structures of a patient.

2. Description of the Related Art

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Apparatuses for performing minimally invasive techniques have been proposed to reduce the trauma of posterior spinal surgery by reducing the size of the incision and the degree of muscle stripping in order to access the vertebrae. One such apparatus provides a constant diameter cannula which is made narrow in order to provide a small entry profile. As a result, the cannula provides minimal space for the physician to observe the body structures and manipulate surgical instruments in order to perform the required procedures. A narrow cannula is typically insufficient to perform one level spinal fixation procedures, which requires visualization of two vertebrae and introduction of screws, rods, as well as other large spinal fixation devices.

In some cases it is desirable to provide treatment of more than two adjacent vertebrae. For example, some conditions require that treatment be made of three adjacent vertebrae, i.e., a "two level procedure." While a narrow constant diameter cannula is typically insufficient for a one level procedure, such a cannula is completely inadequate for a two level procedure. Thus a variety of procedures and combination of procedures requires repeated insertion of multiple cannulae, which eliminates the advantages of minimally invasive procedures.

SUMMARY OF THE INVENTION

Accordingly, there is a need in the art for systems and methods for treating the spine which provide minimally invasive access to the spine such that a variety of procedures, and preferably the entire procedure, can be performed via a single access device.

In one embodiment, a method of treating a spine of a patient is provided. A fusion device is implanted via an anterior approach in an interbody space between at least two of a first vertebra, a second vertebra and a third vertebra. An access device is inserted into the patient with the access device in a first configuration having a first cross-sectional area at a distal portion thereof. The access device is actuated to a second configuration having an enlarged cross-sectional area at the distal portion thereof such that the distal portion extends across at least a portion of each of the three adjacent vertebrae. A multi-level procedure is performed through the access device across the at least three adjacent vertebrae.

In one embodiment, a method of treating a spine of a patient is provided. An interbody space between at least two of a first vertebra, a second vertebra, and a third vertebra is exposed anteriorly. A fusion device is placed in the interbody space. An access device is inserted through an incision in the skin of the patient generally posteriorly until a distal portion thereof is located adjacent the spine. The access device is inserted in a first configuration. The first configuration has a first cross-sectional area at a distal portion thereof. The access device is actuated to a second configuration. The second configuration has an enlarged cross-sectional area at the distal portion thereof. A first fastener configured for insertion into the patient through the access device and for attachment to the first vertebra is provided. A second fastener configured for insertion into the patient through the access device and for attachment to a second vertebra is provided. A third fastener configured for insertion into the internal passage of the expandable conduit and for attachment to a third vertebra is provided. The first, second, and third fasteners are attached to the first, second, and third vertebrae. An elongated member is inserted through the access device and is moved adjacent to the first, second, and third fasteners. The elongate member is secured to the first, second, and third fasteners.

In another embodiment, a method of treating a spine of a patient is provided. An interbody space between at least two of a first vertebra, a second vertebra, and a third vertebra is exposed anteriorly. A fusion device is placed in the interbody space. An access device is inserted through an incision in the skin of the patient generally posteriorly until a distal portion thereof is located adjacent the spine. The access device is inserted in a first configuration. The first configuration has a first cross-sectional area at a distal portion thereof. The access device is actuated to a second configuration that has an enlarged cross-sectional area at the distal portion thereof. A decompression tool is advanced through the access device. A portion of bone is removed from at least one of the first, second, and the third vertebrae through the access device. A first fastener configured for insertion into the patient through the access device and for attachment to the first vertebra is provided. A second fastener configured for insertion into the patient through the access device and for attachment to a second vertebra is provided. A third fastener configured for insertion into the internal passage of the expandable conduit and for attachment to a third vertebra is provided. The first, second, and third fasteners are attached to the first, second, and third vertebrae. An elongated member is inserted through the access device and is moved adjacent to the first, second, and third fasteners. The elongate member is secured to the first, second, and third fasteners.

In another embodiment, a method of treating a spine of a patient is provided. An interbody space between at least two of a first vertebra, a second vertebra, and a third vertebra is exposed. A fusion device is placed in the interbody space. An access device is inserted through an incision in the skin of the patient generally posteriorly until a distal portion thereof is located adjacent the spine. The access device is inserted in a first configuration having a first cross-sectional area at a distal portion thereof. The access device is actuated to a second configuration having an enlarged cross-sectional area at the distal portion thereof. A first fastener configured for insertion into the patient through the access device and for attachment to the first vertebra is provided. A second fastener configured for insertion into the patient through the access device and for attachment to a second vertebra is provided. A third fastener configured for insertion into the internal passage of the expandable conduit and for attachment to a third vertebra is provided. The first, second, and third fasteners are attached to the first, second, and third vertebrae. An elongated member is inserted through the access device and is moved adjacent to the first, second, and third fasteners. The elongate member is secured to the first, second, and third fasteners. A bone growth substance is placed through the access device and adjacent at least one of the first, second, and third fasteners and the elongate member to enhance bone growth.

In another embodiment, a method of treating a spine of a patient is provided. An interbody space between at least two of a first vertebra, a second vertebra, and a third vertebra is exposed anteriorly. A fusion device is placed in the interbody space. An access device is inserted through an incision in the skin of the patient generally posteriorly until a distal portion thereof is located adjacent the spine. The access device is inserted in a first configuration having a first cross-sectional area at a distal portion thereof. The access device is actuated to a second configuration having an enlarged cross-sectional area at the distal portion thereof. A bone growth substance is placed through the access device and adjacent an interbody space defined between at least two of the first, second, and third vertebrae to enhance bone growth therebetween.

In another embodiment, another method of treating a spine of a patient is provided. An access device is through an incision in the skin of the patient generally posteriorly until a distal portion thereof is located adjacent the spine. The access device is inserted in a first configuration having a first cross-sectional area at a distal portion thereof. The access device is actuated to a second configuration that has an enlarged cross-sectional area at the distal portion thereof. The enlarged configuration spans at least a portion of a first vertebra, a second vertebra, and a third vertebra. A fusion device is placed through the access device and in at least one of a first interbody space between the first and second vertebrae and a second interbody space between the second and third vertebrae. A bone growth substance is placed through the access device and adjacent at least one of the first interbody space and the second interbody space to enhance bone growth therebetween.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 2 is a perspective view of one embodiment of an expandable conduit in a reduced profile configuration;

FIG. 3 is a perspective view of the expandable conduit of FIG. 2 in a first enlarged configuration;

FIG. 4 is a perspective view of the expandable conduit of FIG. 2 in a second enlarged configuration;

FIG. 7 is a perspective view of another embodiment of an expandable conduit in an enlarged configuration;

FIG. 8 is an enlarged sectional view of the expandable conduit of FIG. 7 taken along lines 8-8 of FIG. 7;

FIG. 9 is a sectional view of the expandable conduit of FIG. 7 taken along lines 9-9 of FIG. 7;

FIG. 10 is a perspective view of another embodiment of an expandable conduit in an enlarged configuration;

FIG. 11 is an enlarged sectional view of the expandable conduit of FIG. 10 taken along lines 11-11 of FIG. 10;

FIG. 12 is a sectional view of the expandable conduit of FIG. 10 taken along lines 12-12 of FIG. 10;

FIG. 22 is a side view of the endoscope mount platform of FIG. 20 illustrated with one embodiment of an indexing arm and one embodiment of an endoscope;

FIG. 23 is a perspective view of one embodiment of an indexing collar of the endoscope mount platform FIG. 20;

FIG. 27(a) is an enlarged side view of one embodiment of a biasing member illustrated in FIG. 27 taken from the perspective of the arrow 27a;

FIG. 28 is a perspective view of one embodiment of a surgical instrument;

FIG. 29 is an enlarged sectional view of the fastener of FIGS. 26-27 coupled with the surgical instrument of FIG. 28, illustrating one embodiment of a stage of one embodiment of a method for treating the spine of a patient;

FIG. 30 is side view of one embodiment of another surgical instrument;

FIG. 31 is a partial sectional view of one embodiment of a stage of one embodiment of a method for treating the spine of a patient;

FIG. 32 is a side view of one embodiment of another surgical instrument;

FIG. 33 is a perspective view similar to FIG. 31 illustrating the apparatuses of FIGS. 26 and 32, in one embodiment of a stage of one embodiment of a method for treating the spine of a patient;

FIG. 34 is an enlarged sectional view of the apparatus of FIGS. 26 and 32, illustrating one embodiment of a stage of one embodiment of a method for treating the spine of a patient;

FIG. 36 is an enlarged view in partial section illustrating one embodiment of a stage of one embodiment of a method for treating the spine of a patient; and FIG. 37 is a partial view of illustrating one embodiment of a stage of one embodiment of a method for treating the spine of a patient.

Figure 1:
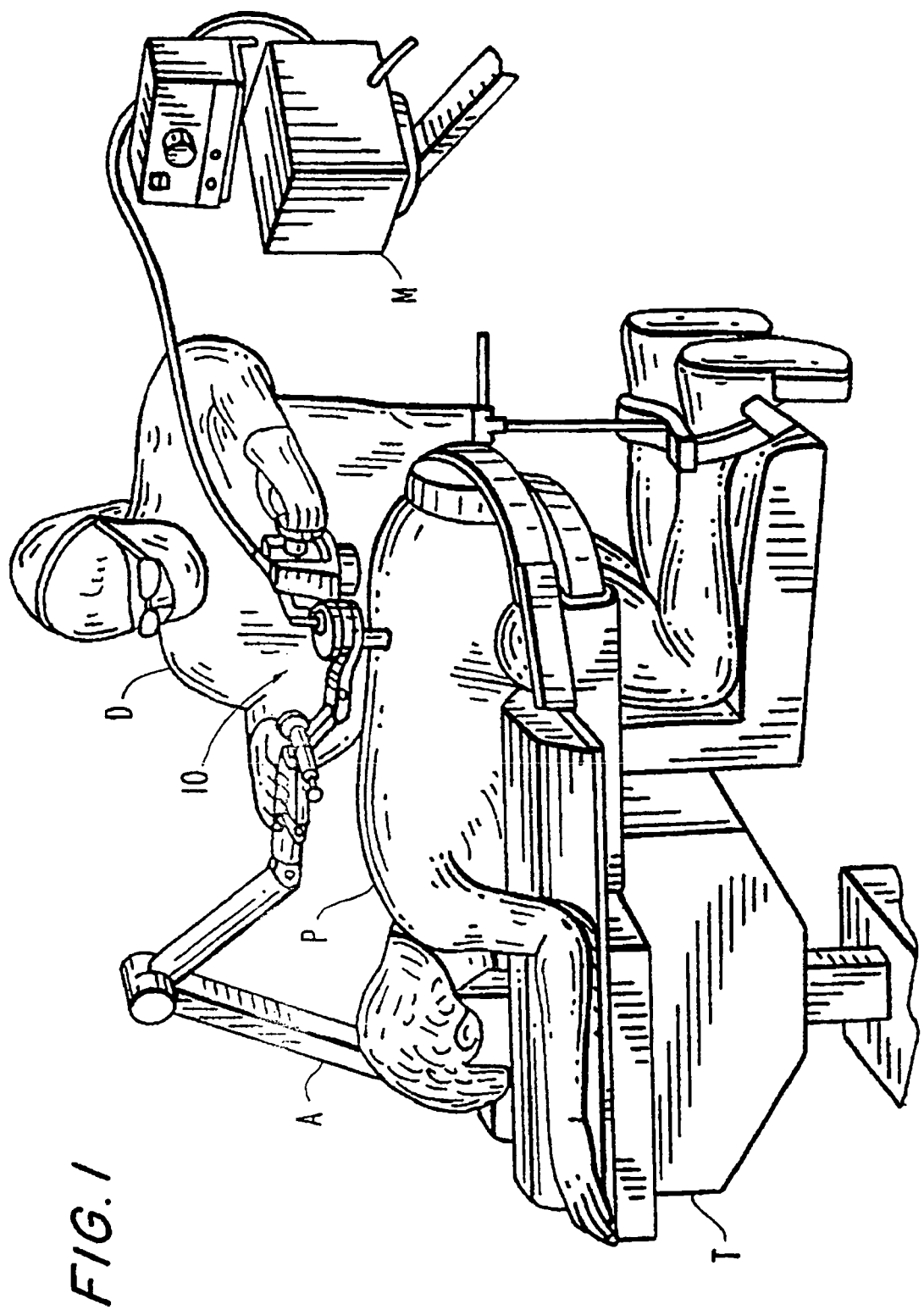
FIG. 1 is a perspective view of one embodiment of a surgical system and one embodiment of a method for treating the spine of a patient.
Figure 6:
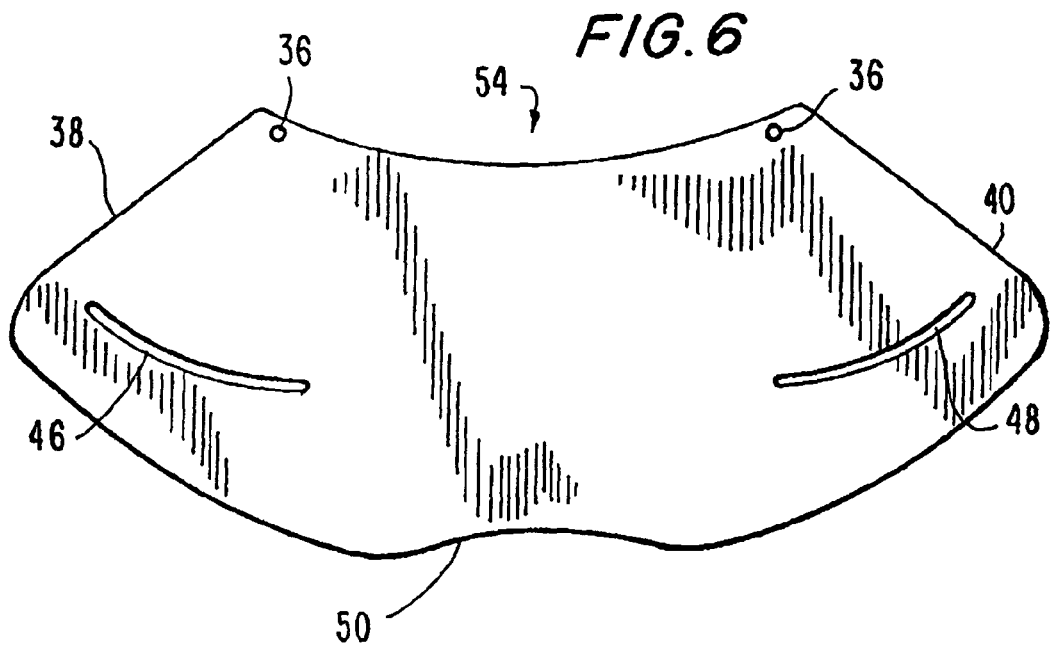
FIG. 6 is a view of another embodiment of a skirt portion of an expandable conduit.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

As should be understood in view of the following detailed description, this application is directed to apparatuses and methods for treating the spine of a patient through an access device, also referred to herein as an expandable conduit. More particularly, the systems described below provide access to surgical locations at or near the spine and provide a variety of tools useful in performing treatment of the spine. Also, the systems described herein enable a surgeon to perform a wide variety of methods as described herein.

I. Systems for Performing Procedures at a Surgical Location

Various embodiments of apparatuses and procedures described herein will be discussed in terms minimally invasive procedures and apparatuses, e.g., of endoscopic apparatuses and procedures. However, many aspects of the present invention may find use in conventional, open, and mini-open procedures. In the drawings and description which follows, the term "proximal," as is traditional, refers to the end portion of the apparatus which is closest to the operator, while the term "distal" will refer to the end portion which is farthest from the operator.

FIG. 1 shows one embodiment of a surgical system 10 that can be used to perform a variety of methods or procedures. In at least a portion of the procedure, as discussed more fully below, the patient P typically is placed in the prone position on operating table T, taking care that the abdomen is not compressed and physiological lordosis is preserved, as is known in the art. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006.

Visualization of the surgical site may be achieved in any suitable manner, e.g., by use of a viewing element, such as an endoscope, a camera, loupes, a microscope, direct visualization, or any other suitable viewing element, or a combination of the foregoing. In one embodiment, the viewing element provides a video signal representing images, such as images of the surgical site, to a monitor M. The viewing element may be an endoscope and camera which captures images to be displayed on the monitor M whereby the physician D is able to view the surgical site as the procedure is being performed. The endoscope and camera will be described in greater detail herein.

The systems and procedures will be described herein in connection with minimally invasive postero-lateral spinal surgery. One such method is a two level postero-lateral fixation of the spine involving the L4, L5, and S1 vertebrae. (In the drawings, the vertebrae will generally be denoted by reference letter V.) The usefulness of the apparatuses and procedures is neither restricted to the postero-lateral approach nor to the L4, L5, and S1 vertebrae, but it may be used in other anatomical approaches and other vertebra(e) within the cervical, thoracic, and lumbar regions of the spine. The procedures may be directed toward surgery involving one or more vertebral levels. It is also useful for anterior and lateral procedures. Moreover, it is believed that the invention is also particularly useful where any body structures must be accessed beneath the skin and muscle tissue of the patient, and where it desirable to provide sufficient space and visibility in order to manipulate surgical instruments and treat the underlying body structures. For example, certain features or instrumentation described herein are particularly useful for a minimally invasive procedures, e.g., arthroscopic procedures. As discussed more fully below, one embodiment of an apparatus described herein provides an expandable conduit that has an expandable distal portion. The expandable distal portion prevents or substantially prevents the expandable conduit or instruments extended therethrough to the surgical site from being dislodging or popping out of the operative site.

The system 10 includes an expandable conduit or access device that provides a internal passage for surgical instruments to be inserted through the skin and muscle tissue of the patient P to the surgical site. The expandable conduit has a wall portion defining reduced profile configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the expandable conduit therein.

The wall portion of the expandable conduit is subsequently expanded to an enlarged configuration, by moving against the surrounding muscle tissue to at least partially define an enlarged surgical space in which the surgical procedures will be performed. In a sense, it acts as its own dilator. The expandable conduit may also be thought of as a retractor, and may be referred to herein as such. Typically, but not by way of limitation, the distal portion expands to a greater extent than the proximal portion, because the surgical procedures are to be performed at the surgical site which is adjacent the distal portion when the expandable conduit is inserted into the patient.

While in the reduced profile configuration, the expandable conduit defines a first unexpanded configuration. Thereafter, the expandable conduit enlarges the surgical space defined thereby by engaging the tissue surrounding the conduit and displacing the tissue radially outwardly as the conduit expands. The expandable conduit may be sufficiently rigid to displace such tissue during the expansion thereof. The expandable conduit may be resiliently biased to expand from the reduced profile configuration to the enlarged configuration. In addition, the conduit may also be manually expanded by an expander device with or without one or more surgical instruments inserted therein, as will be described below. The surgical site is at least partially defined by the expanded conduit itself. During expansion, the conduit moves from the first overlapping configuration to a second overlapping configuration.

In addition to enlargement, the distal end portion of the expandable conduit may be configured for relative movement with respect to the proximal end portion in order to allow the physician to precisely position the distal end portion at the desired location. This relative movement also provides the advantage that the proximal portion of the expandable conduit nearest the physician D may remain substantially stable during such distal movement. In an exemplary embodiment, the distal portion is a separate component which is pivotably or movably attached relative to the proximal portion. In another embodiment, the distal portion is flexible or resilient in order to permit such relative movement.

One embodiment of an expandable conduit is illustrated in FIGS. 2-6 and designated by reference number 20. The expandable conduit 20 includes a proximal wall portion 22, which has a tubular configuration, and a distal wall portion, which is an expandable skirt portion 24. The skirt portion 24 is enlargeable from a reduced profile configuration having an initial dimension 26 and corresponding cross-sectional area (illustrated in FIG. 2), to an enlarged configuration having a dimension 28 and corresponding cross-sectional area (illustrated in FIG. 4). In one embodiment, the skirt portion 24 is attached to the proximal wall portion 22 with a rivet 30, pin, or similar connecting device to permit movement of the skirt portion 24 relative to the proximal wall portion 22.

In the illustrated embodiment, the skirt portion 24 is manufactured from a resilient material, such as stainless steel. The skirt portion 24 is manufactured so that it normally assumes an expanded configuration illustrated in FIG. 4. As illustrated in FIG. 3, the skirt portion 24 may assume an intermediate dimension 34 and corresponding cross-sectional area, which is greater than the dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 will depend upon several factors, including the rigidity of the skirt portion 24, the surrounding tissue, and whether such surrounding tissue has relaxed or tightened during the course of the procedure. An outer plastic sleeve 32 (illustrated in dashed line in FIG. 2) may be provided which surrounds the expandable conduit 20 and maintains the skirt portion 24 in the reduced profile configuration. The outer sleeve 32 may have a braided polyester suture embedded within it (not shown), aligned substantially along the longitudinal axis thereof; such that when the suture is withdrawn, the outer sleeve 32 is torn, which allows the expandable conduit 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 is sufficiently rigid that it is capable of displacing the tissue surrounding the skirt portion 24 as it expands. Depending upon the resistance exerted by surrounding tissue, the skirt portion is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion creates a stable configuration that is at least temporarily stationary in the patient, which frees the physician from the need to actively support the conduit 20 until an endoscope mount platform 300 and a support arm 400 are subsequently added in one embodiment (see FIGS. 21-22).

Figure 5:
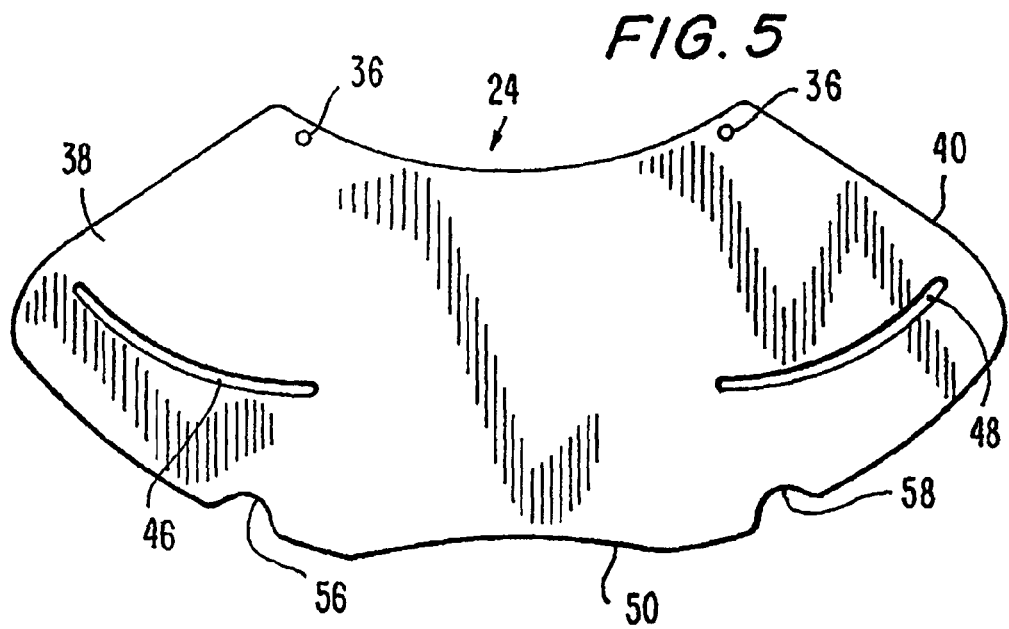
FIG. 5 is a view of one embodiment of a skirt portion of an expandable conduit.

The skirt portion 24 of the expandable conduit 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. As discussed above, the unrestricted shape of the skirt portion 24 preferably is a circular or an oblong shape. The skirt portion 24 may also take on an oval shape, wherein the dimension 28 would define a longer dimension the skirt portion 24 and would be about 85 mm in one embodiment. In another embodiment, the skirt portion 24 has an oval shape and the dimension 28 defines a longer dimension of the skirt portion 24 and would be about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 is attached to the proximal wall portion 22 with a pivotable connection, such as rivet 30. A pair of rivet holes 36 are provided in the skirt portion 24 to receive the rivet 30. The skirt portion 24 also has two free ends 38 and 40 in one embodiment that are secured by a slidable connection, such as second rivet 44 (not shown in FIG. 5, illustrated in FIGS. 2-4). A pair of complementary slots 46 and 48 are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. However, the likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span as many as three vertebrae, e.g., L4, L5, and S1, to perform multi-level fixation alone or in combination with a variety of other procedures, as discussed below.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58, are provided, as illustrated in FIG. 5. When the skirt portion 24 is assembled, the notched portions 56 and 58 are oriented in the cephcaudal direction (indicated by an arrow 60 in FIG. 4) and permit instrumentation, such as an elongated member 650 used in a fixation procedure (described in detail below), to extend beyond the area enclosed by the skirt portion 24 without moving or raising the skirt portion 24 from its location to allow the elongated member 650 to pass under the skirt portion 24. The notched portions 56, 58 are optional, as illustrated in connection with another embodiment of an expandable conduit 54, illustrated in FIG. 6, and may be eliminated where the physician deems the notches to be unnecessary for the procedures to be performed (e.g., where fixation does not require extended access, as discussed more fully below.)

As illustrated in FIG. 4, the skirt portion 24 may be expanded to a substantially conical configuration having a substantially circular or elliptical profile. In another embodiment, features may be provided on the skirt portion which facilitate the bending of the skirt portion at several locations to provide a pre-formed enlarged configuration. For example, another embodiment of an expandable conduit 70, illustrated in FIGS. 7-9, provides a skirt portion 74 that has four sections 76a, 76b, 76c, 76d having a reduced thickness. For a skirt portion 74 having a thickness 78 of about 0.007 inches, reduced thickness sections 76a, 76b, 76c, 76d may have a thickness 80 of about 0.002-0.004 inches (FIG. 8). The reduced thickness sections 76a, 76b, 76c, 76d may have a width 82 of about 1-5 mm. The thickness 78 of the skirt portion 74 may be reduced by milling or grinding, as is known in the art. When the skirt portion 74 is opened, it moves toward a substantially rectangular configuration, as shown in FIG. 9, subject to the resisting forces of the body tissue. In another embodiment (not shown), a skirt portion may be provided with two reduced thickness sections (rather than the four reduced thickness sections of skirt 74) which would produce a substantially "football"-shaped access area.

FIGS. 10-12 show another embodiment of an expandable conduit 80. The expandable conduit 80 has a skirt portion 84 with a plurality of perforations 86. The perforations 86 advantageously increase the flexibility at selected locations. The size and number of perforations 86 may vary depending upon the desired flexibility and durability. In another embodiment, the skirt portion 84 may be scored or otherwise provided with a groove or rib in order to facilitate the bending of the skirt portion at the desired location.

Figure 13:
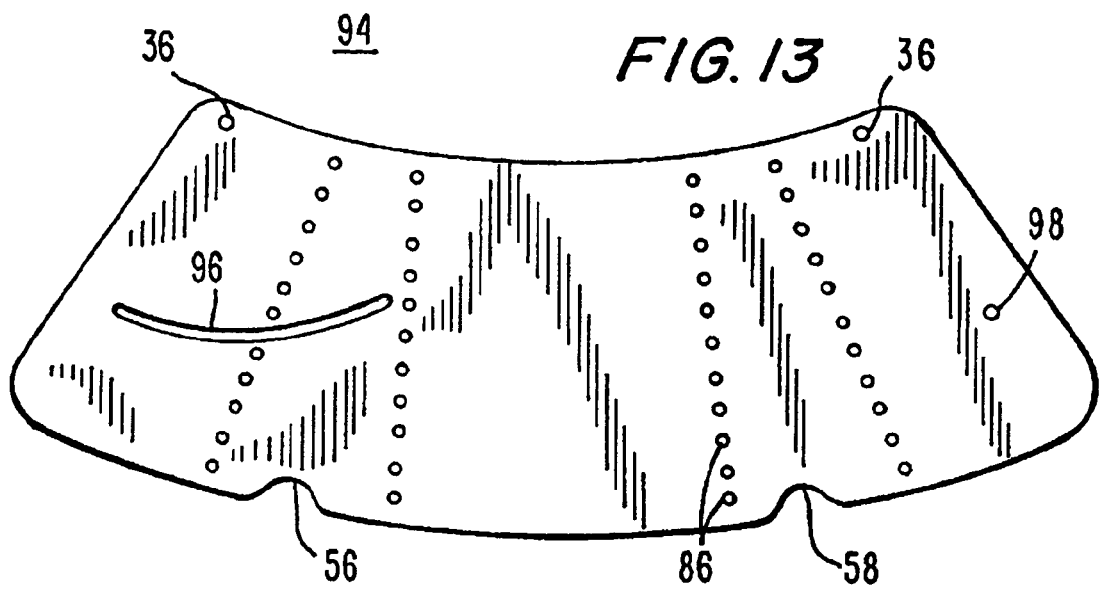
FIG. 13 is a view of a portion of another embodiment of the expandable conduit.
Figure 14:
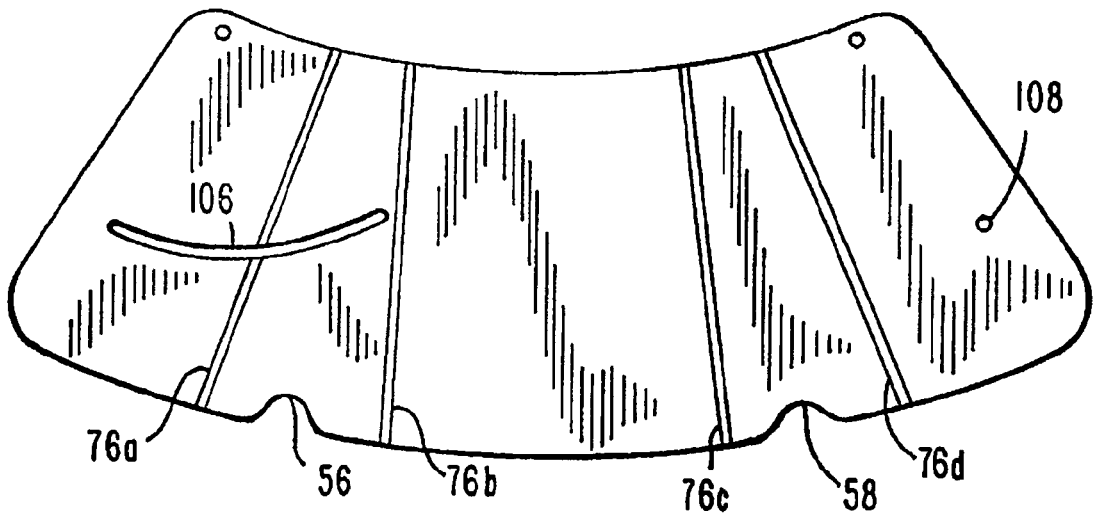
FIG. 14 is a view of a portion of another embodiment of the expandable conduit.

FIG. 13 illustrates another embodiment of an expandable conduit that has a skirt portion 94 having one slot 96 and an aperture 98. A rivet (not shown) is stationary with respect to the aperture 98 and slides within the slot 96. FIG. 14 illustrates another embodiment of an expandable conduit that has a skirt portion 104 that includes an aperture 108. The apertures 108 receives a rivet (not shown) that slides within elongated slot 106.

Further details of the expandable conduit are described in U.S. Pat. No. 6,187,00, and in U.S. patent application Ser. No. 09/772,605, filed Jan. 30, 2001, U.S. application Ser. No. 10/361,887 filed Feb. 10, 2003, and application Ser. No. 10/280,489 filed Oct. 25, 2002, which are incorporated by reference in their entirety herein.

In one embodiment of a procedure, an early stage involves determining a point in the skin of the patient at which to insert the expandable conduit. The access point preferably corresponds to the posterior-lateral aspects of the spine. Manual palpation and Anterior-Posterior (AP) fluoroscopy may be used to determine preferred or optimal locations for forming an incision in the skin of the patient. In one embodiment, the expandable conduit 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, without damaging the structure of surrounding tissue and muscles. A first dilator is placed over the guide wire, which expands the opening. The guide wire is then subsequently removed. A second dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. In one embodiment of the method, desired opening size is about 23 mm. (Other dimensions of the opening, e.g., about 20 mm, 27 mm, 30 mm, etc., are also useful with this apparatus in connection with spinal surgery, and still other dimensions are contemplated.)

Figure 15:
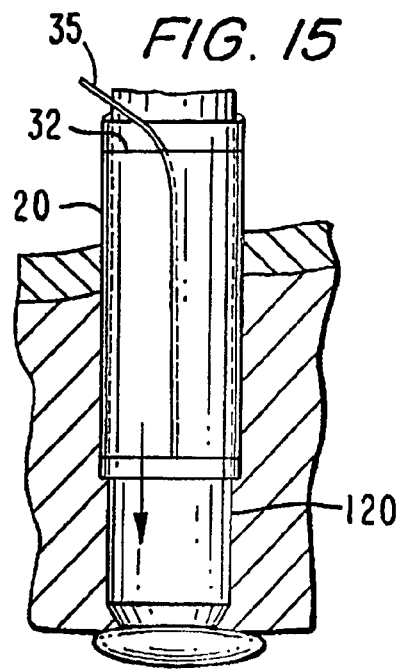
FIG. 15 is a sectional view illustrating one embodiment of a stage of one embodiment of a method for treating the spine of a patient.

FIG. 15 shows that following placement of a dilator 120, which is the largest dilator in the above-described dilation process, the expandable conduit 20 is introduced in its reduced profile configuration and positioned in a surrounding relationship over the dilator 120. The dilator 120 is subsequently removed from the patient, and the expandable conduit 20 is allowed to remain in position.

Once positioned in the patient, the expandable conduit 20 may be enlarged to provide a passage for the insertion of various surgical instruments and to provide an enlarged space for performing the procedures described herein. As described above, the expandable conduit may achieve the enlargement in several ways. In one embodiment, a distal portion of the conduit may be enlarged, and a proximal portion may maintain a constant diameter. The relative lengths of the proximal portion 22 and the skirt portion 24 may be adjusted to vary the overall expansion of the conduit 20. Alternatively, such expansion may extend along the entire length of the expandable conduit 20. In one embodiment of a procedure, the expandable conduit 20 may be expanded by removing a suture 35 and tearing the outer sleeve 32 surrounding the expandable conduit 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 allow the expandable conduit 20 to resist closing to the reduced profile configuration of FIG. 2 and to at least temporarily resist being expelled from the incision. These characteristics create a stable configuration for the conduit 20 to remain in position in the body, supported by the surrounding tissue. It is understood that additional support may be needed, especially if an endoscope is added.

According to one embodiment of a procedures, the expandable conduit 20 may be further enlarged at the skirt portion 24 using an expander apparatus to create a surgical access space. An expander apparatus useful for enlarging the expandable conduit has a reduced profile configuration and an enlarged configuration. The expander apparatus is inserted into the expandable conduit in the reduced profile configuration, and subsequently expanded to the enlarged configuration. The expansion of the expander apparatus also causes the expandable conduit to be expanded to the enlarged configuration. In some embodiments, the expander apparatus may increase the diameter of the expandable conduit along substantially its entire length in a conical configuration. In other embodiments, the expander apparatus expands only a distal portion of the expandable conduit, allowing a proximal portion to maintain a constant diameter.

In addition to expanding the expandable conduit, the expander apparatus may also be used to position the distal portion of the expandable conduit at the desired location for the surgical procedure. The expander engages an interior wall of the expandable conduit, and moves the conduit to the proper location. For the embodiments in which the distal portion of the expandable conduit is relatively movable with respect to the proximal portion, the expander apparatus is useful to position the distal portion without substantially disturbing the proximal portion.

Figure 17:
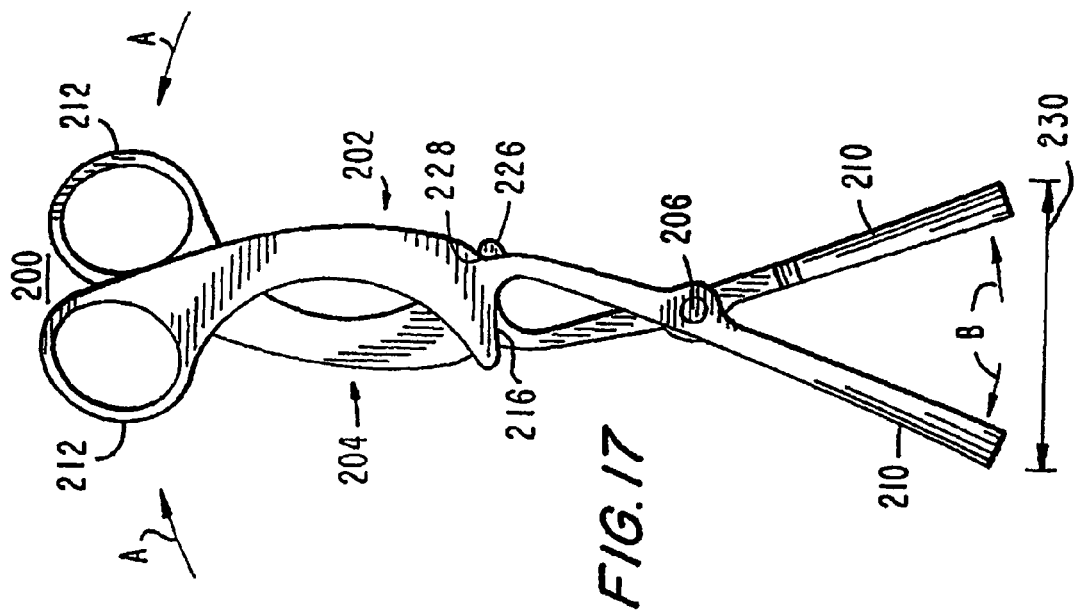
FIG. 17 is a side view of the expander apparatus of FIG. 16 in an expanded configuration.
Figure 16:
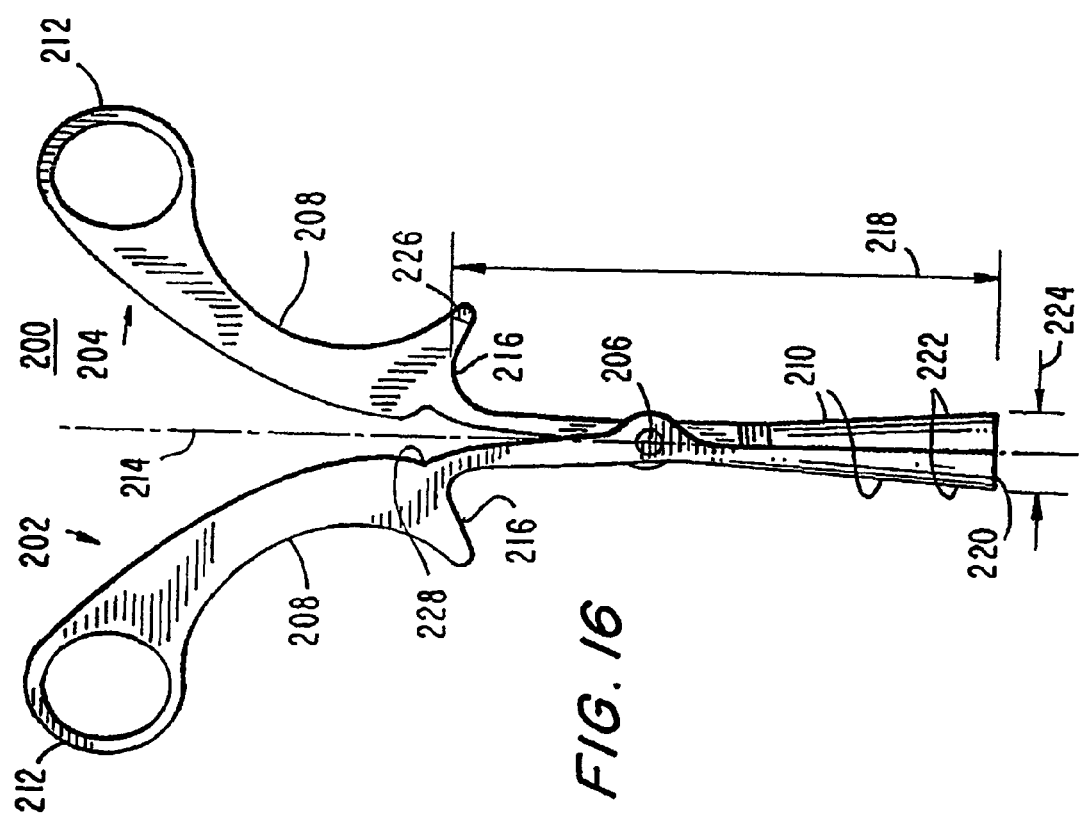
FIG. 16 is a side view of one embodiment of an expander apparatus in a reduced profile configuration.
Figure 20:
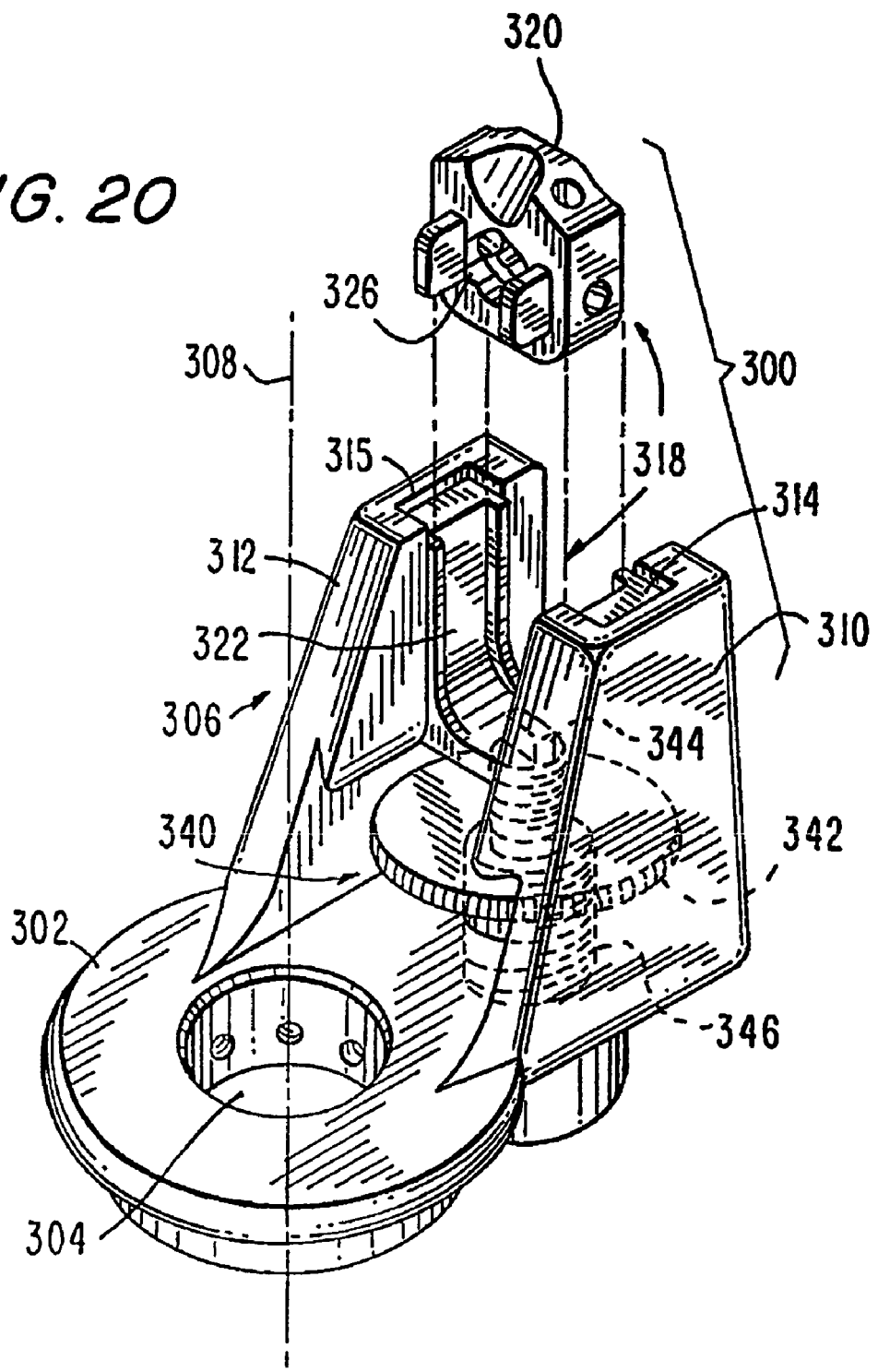
FIG. 20 is an exploded perspective view of one embodiment of an endoscope mount platform.

In some procedures, an expander apparatus is used to further expand the skirt portion 24 towards the enlarged configuration (illustrated in FIG. 4). The expander apparatus is inserted into the expandable conduit, and typically has two or more members which are movable to engage the interior wall of the skirt portion 24 and apply a force sufficient to further expand the skirt portion 24. FIGS. 16 and 17 show one embodiment of an expander apparatus 200 that has a first component 202 and a second component 204. a first component 202 and a second component 204 of the expander apparatus 200 are arranged in a tongs-like configuration and are pivotable about a pin 206. The first and second components 202 and 204 are typically constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 is dimensioned to engage the proximal end 25 of the expandable conduit 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the typical depth of the body structures beneath the skin surface at which the surgical procedure is being performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by an arrow A in FIG. 17, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the expandable conduit 20 beyond its designed dimension, and to minimize trauma to the underlying tissue. Further details of the expander apparatus are described in U.S. patent application Ser. No. 09/906,463 filed Jul. 16, 2001, which is incorporated by reference in their entirety herein.

When the expandable conduit 20 is inserted into the patient and the outer sleeve 32 is removed, the skirt portion 24 expands to a point where the outward resilient expansion of the skirt portion 24 is balanced by the force of the surrounding tissue. The surgical space defined by the conduit may be sufficient to perform any of a number of surgical procedures or combination of surgical procedures described herein. However, if it is desired to expand the expandable conduit 20 further, the expander apparatus 200 may be inserted into the expandable conduit 20 in the reduced profile configuration until the shoulder portions 216 are in approximation with the proximal end 25 of the skirt portion 24 of the expandable conduit 20, as shown in FIG. 18.

Figure 18:
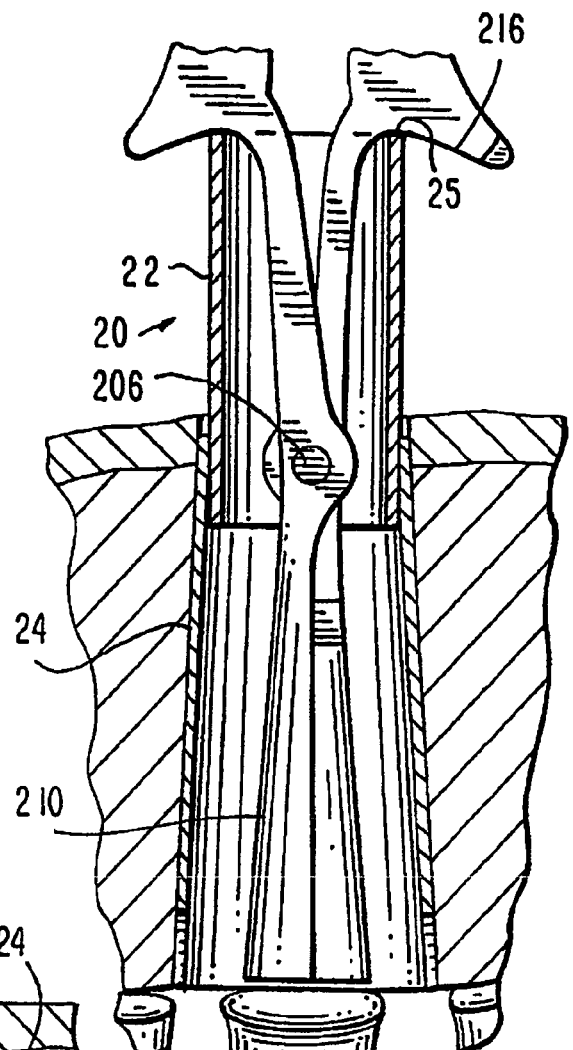
FIG. 18 is a sectional view of the expander apparatus of FIGS. 16-17 inserted into the expandable conduit of FIG. 2, which has been inserted into a patient.
Figure 19:
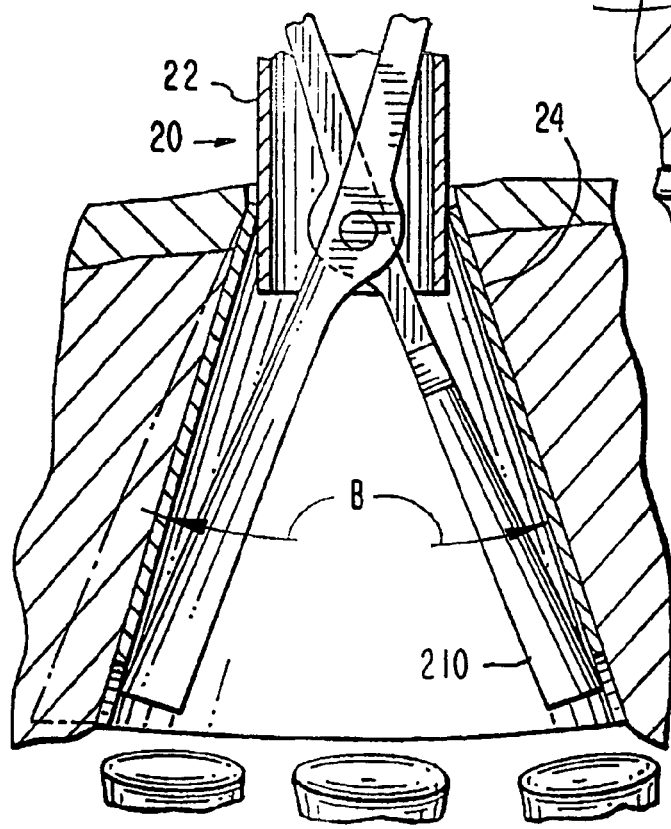
FIG. 19 is a sectional view of the expander apparatus of FIGS. 16-17 inserted into the expandable conduit of FIG. 2 and expanded to the expanded configuration to retract tissue.

FIG. 18 shows the expander apparatus 200 is inserted in the expandable conduit 20 in the reduced profiled configuration. Expansion of the expander apparatus 200 is achieved by approximating the handle portions 212 (not shown in FIG. 18), which causes the distal portions 210 of the expander apparatus 200 to move to a spaced apart configuration. As the distal portions 210 move apart and contact the inner wall of the skirt portion 24, the skirt portion 24 is expanded by allowing the rivet 44 to slide within the slots 46 and 48 of the skirt portion 24. When the distal portions 210 reach the maximum expansion of the skirt portion 24 (illustrated by a dashed line in FIG. 19), the tab 226 and shoulder portion 228 of the expander apparatus 200 come into engagement to prevent further expansion of the tong portions (as illustrated in FIG. 17). The conduit 20 may be alternatively further expanded with a balloon or similar device.

A subsequent, optional step in the procedure is to adjust the location of the distal portion of the expandable conduit 20 relative to the body structures to be operated on. For example, the expander apparatus 200 may also be used to engage the inner wall of the skirt portion 24 of the expandable conduit 20 in order to move the skirt portion 24 of the expandable conduit 20 to the desired location. For an embodiment in which the skirt portion 24 of the expandable conduit 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the expandable conduit, as described below.

An endoscope mount platform 300 and indexing arm 400 provide securement of an endoscope 500 on the proximal end 25 of the expandable conduit 20 for remotely viewing the surgical procedure, as illustrated in FIGS. 20-23. The endoscope mount platform 300 may also provide several other functions during the surgical procedure. The endoscope mount platform 300 includes a base 302 that extends laterally from a central opening 304 in a general ring-shaped configuration. The base 302 provides an aid for the physician, who is primarily viewing the procedure by observing a monitor, when inserting surgical instruments into the central opening 304. For example, the size of the base 302 provides visual assistance (as it may be observable in the physician's peripheral vision) as well as provides tactile feedback as the instruments are lowered towards the central opening 304 and into the expandable conduit 20.

The endoscope mount platform 300 further provides a guide portion 306 that extends substantially parallel to a longitudinal axis 308 away from the central opening 304. The base 302 is typically molded as one piece with the guide portion 306. The base 302 and guide portion 306 may be constructed as a suitable polymer such as polyetheretherketone (PEEK).

The guide portion 306 includes a first upright member 310 that extends upward from the base 302 and a second upright member 312 that extends upward from the base 302. The upright members 310, 312 each have a respective vertical grooves 314 and 315 that can slidably receive an endoscopic mount assembly 318.

The endoscope 500 (not shown in FIG. 20) is movably mounted to the endoscope mount platform 300 by the endoscope mount assembly 318. The endoscope mount assembly 318 includes an endoscope mount 320 and a saddle unit 322. The saddle unit 322 is slidably mounted is within the grooves 314 and 315 in the upright members 310 and 312. The endoscope mount 320 receives the endoscope 500 through a bore 326 which passes through the endoscope mount 320. Part of the endoscope 500 may extend through the expandable conduit 20 substantially parallel to longitudinal axis 308 into the patient's body 130.

The endoscope mount 320 is removably positioned in a recess 328 defined in the substantially "U"-shaped saddle unit 322, which is selectively movable in a direction parallel to the longitudinal axis 308 in order to position the endoscope 500 at the desired height within the expandable conduit 20 to provide a zoom feature to physician's view of the surgical procedure.

A screw mechanism 340 is positioned on the base 302 between the upright members 310 and 312, and is used to selectively move the saddle unit 322, and the endoscope mount 320 and the endoscope 500 which are supported by the saddle unit 322. The screw mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 has a first end received in a rectangular opening in the saddle unit 322, which inhibits rotational movement of the spindle 344. The second end of the spindle 344 has an external thread which cooperates with an internal thread formed in a bore within the thumb wheel 342. Rotation of the thumb wheel 342 relative to the spindle 344, causes relative axial movement of the spindle unit 344 along with the saddle unit 322. Further details of the endoscope mount platform are described in U.S. patent application Ser. No. 09/491,808 filed Jan. 28, 2000, application Ser. No. 09/821,297 filed Mar. 29, 2001, and application Ser. No. 09/940,402 filed Aug. 27, 2001.

Figure 21:
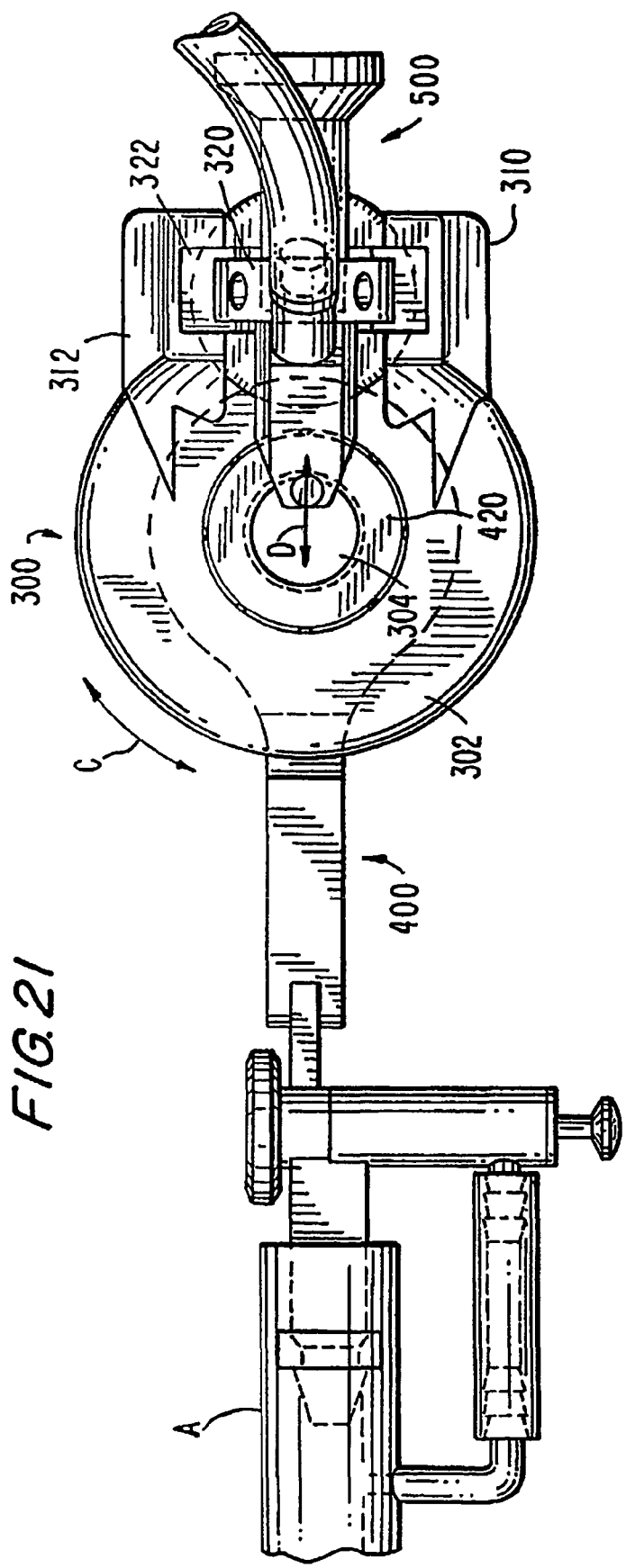
FIG. 21 is a top view of the endoscope mount platform of FIG. 20 coupled with one embodiment of an indexing arm and one embodiment of an endoscope.

FIGS. 21-23 show that the endoscope mount platform 300 is mountable to the support arm 400 in one embodiment. The support arm 400, in turn, preferably is mountable to mechanical support, such as mechanical support arm A, discussed above in connection with FIG. 1. The support arm 400 rests on the proximal end 25 of the expandable conduit 20. The support arm 400 includes an indexing collar 420, which is received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

The collars 420 advantageously make the surgical system 10 a modular in that different expandable conduits 20 may be used with a single endoscope mount platform 300. For example, expandable conduits 20 of different dimensions may be supported by providing of indexing collars 420 to accommodate each conduit size while using a single endoscope mount platform 300. The central opening 304 of the endoscope mount platform 300 has constant dimension, e.g., a diameter of about 32.6 mm. An appropriate indexing collar 420 is selected, e.g., one that is appropriately sized to support a selected expandable conduit 20. Thus the outer wall 422 and the outer diameter 430 are unchanged between different indexing collars 420, although the inner wall 424 and the inner diameter 432 vary to accommodate differently sized conduits 20.

The indexing collar 420 is mounted to the proximal portion of the expandable conduit 20 and allows angular movement of the endoscope mount platform 300 with respect thereto about the longitudinal axis 308 (as indicated by an arrow C in FIG. 21). The outer wall 422 of the index collar 420 includes a plurality of hemispherical recesses 450 that can receive one or more ball plungers 350 on the endoscope mount platform 300 (indicated in dashed line.) This arrangement permits the endoscope mount platform 300, along with the endoscope 500, to be fixed in a plurality of discrete angular positions. Further details of the support arm and indexing collar are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001.

Figure 24:
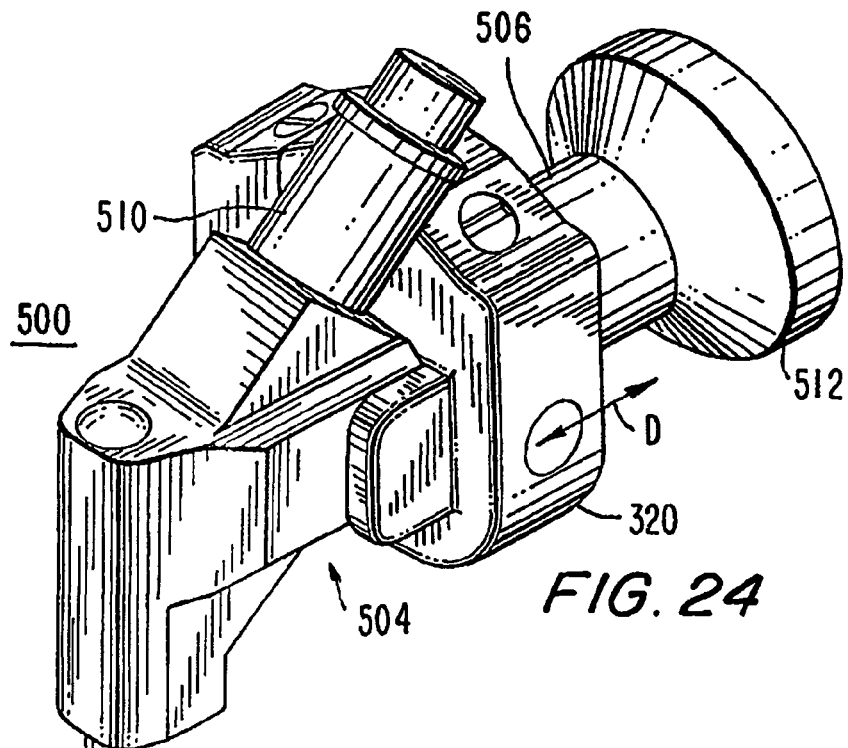
FIG. 24 is a perspective view of one embodiment of an endoscope.

FIG. 24 shows one embodiment of the endoscope 500, which has an elongated configuration that extends into the expandable conduit 20 in order to view the surgical site. In particular, the endoscope 500 has an elongated rod portion 502 and a body portion 504 which is substantially perpendicular thereto. In the illustrated embodiment, the rod portion 502 of endoscope 500 has a diameter of about 4 mm and a length of about 106 mm. Body portion 504 may define a tubular portion 506 which is configured to be slidably received in the bore 326 of endoscope mount 320 as indicated by an arrow D. The slidable mounting of the endoscope 500 on the endoscope mount platform 300 permits the endoscope 500 to adjust to configurations that incorporate different conduit diameters. Additional mobility of the endoscope 500 in viewing the surgical site may be provided by rotating the endoscope mount platform 300 about the central axis 308 (as indicated by arrow C in FIG. 21).

The rod portion 502 supports an optical portion (not shown) at a distal end 508 thereof, which may define a field of view of about 105 degrees and a direction of view 511 of about 25-30 degrees. An eyepiece 512 is positioned at an end portion of the body portion 504. A camera (not shown) preferably is attached to the endoscope 500 adjacent the eyepiece 512 with a standard coupler unit. A light post 510 supplies illumination to the surgical site at the distal end portion 508. A preferred camera for use in the system and procedures described herein is a three chip unit that provides greater resolution to the viewed image than a single chip device.

Figure 25:
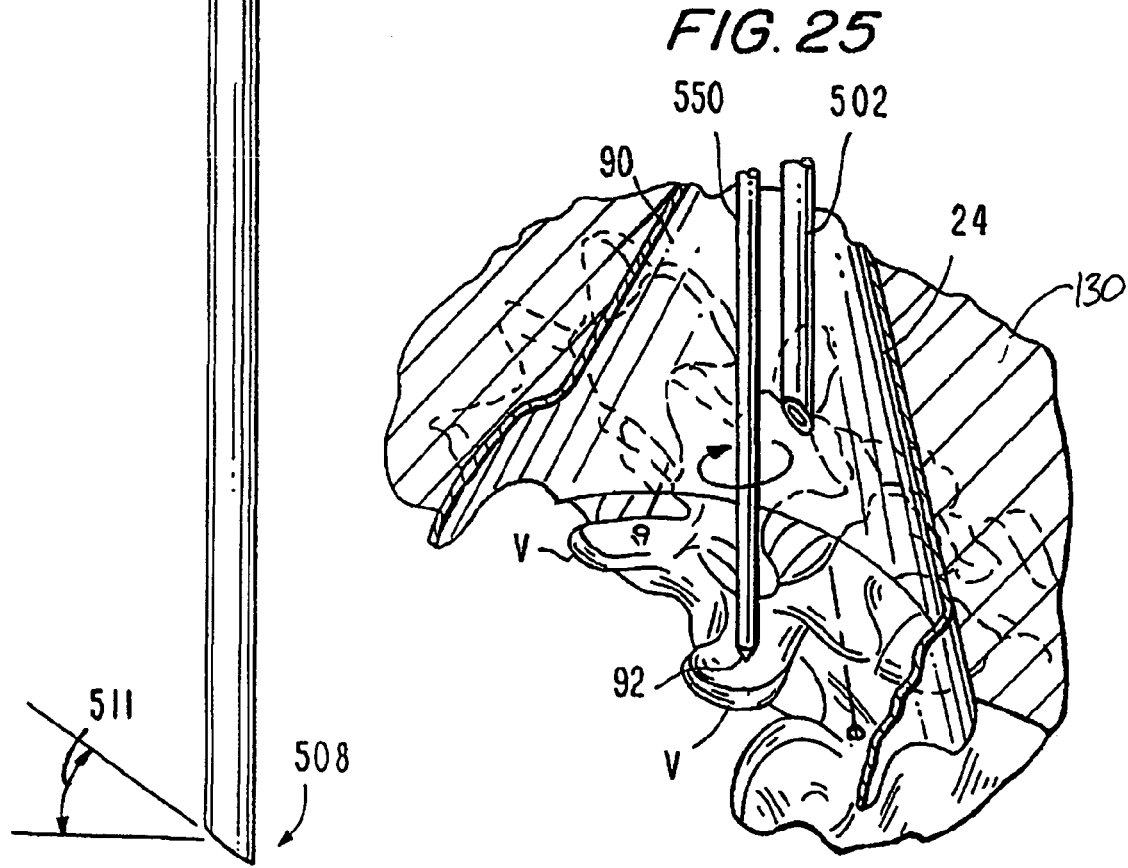
FIG. 25 is a partial sectional view of one embodiment of a stage of one embodiment of a method for treating the spine of a patient.

A subsequent stage in the procedure involves placing the support arm 400 and the endoscope mount platform 300 on the proximal portion, e.g., the proximal end 25, of the expandable conduit 20 (FIGS. 1 and 22), and mounting of the endoscope 500 on the endoscope mount platform 300. A next step is insertion of one or more surgical instruments into the expandable conduit 20 to perform the surgical procedure on the body structures at least partially within the operative space defined by the expanded portion of the expandable conduit. FIG. 25 shows that in one method, the skirt portion 24 of expandable conduit 20 at least partially defines a surgical site or operative space 90 in which the surgical procedures described herein may be performed. Depending upon the overlap of the skirt portion, the skirt portion may define a surface which is continuous about the circumference or which is discontinuous having one or more gaps where the material of the skirt portion does not overlap.

One procedure performable through the expandable conduit 20, described in greater detail below, is a two-level spinal fixation. Surgical instruments inserted into the expandable conduit may be used for debridement and decortication. In particular, the soft tissue, such as fat and muscle, covering the vertebrae may be removed in order to allow the physician to visually identify the various "landmarks," or vertebral structures, which enable the physician to locate the location for attaching a fastener, such a fastener 600, discussed below, or other procedures, as will be described herein. Allowing visual identification of the vertebral structures enables the physician to perform the procedure while viewing the surgical area through the endoscope, microscope, loupes, etc., or in a conventional, open manner.

Tissue debridement and decortication of bone are completed using one or more debrider blades, bipolar sheath, high speed burr, and additional conventional manual instruments. The debrider blades are used to excise, remove and aspirate the soft tissue. The bipolar sheath is used to achieve hemostasis through spot and bulk tissue coagulation. The debrider blades and bipolar sheath are described in greater detail in U.S. Pat. No. 6,193,715, assigned to Medical Scientific, Inc., which is incorporated by reference in its entirety herein. The high speed burr and conventional manual instruments are also used to continue to expose the structure of the vertebrae.

A subsequent stage is the attachment of fasteners to the vertebrae V. Prior to attachment of the fasteners, the location of the fastener attachment is confirmed. In the exemplary embodiment, the pedicle entry point of the L5 vertebrae is located using visual landmarks as well as lateral and A/P fluoroscopy, as is known in the art. With continued reference to FIG. 25, the entry point 92 is prepared with an awl 550. The pedicle hole 92 is completed using instruments known in the art such as a straight bone probe, a tap, and a sounder. The sounder, as is known in the art, determines whether the hole that is made is surrounded by bone on all sides, and that there has been no perforation of the pedicle wall.

After hole in the pedicle is provided at the entry point 92 (or at any point during the procedure), an optional step is to adjust the location of the distal portion of the expandable conduit 20. This may be performed by inserting the expander apparatus 200 into the expandable conduit 20, expanding the distal portions 210, and contacting the inner wall of the skirt portion 24 to move the skirt portion 24 to the desired location. This step may be performed while the endoscope 500 is positioned within the expandable conduit 20, and without substantially disturbing the location of the proximal portion of the expandable conduit 20 to which the endoscope mount platform 300 may be attached.

Figure 26:
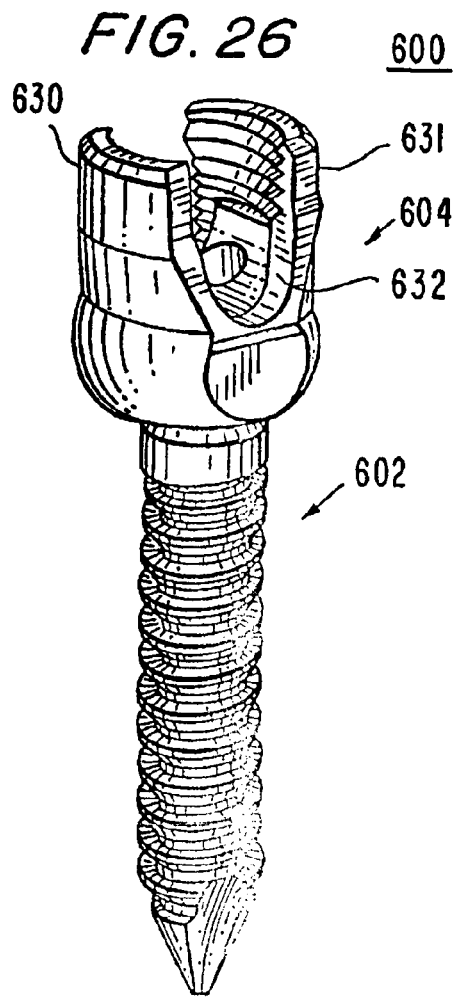
FIG. 26 is a perspective view of one embodiment of a fastener.
Figure 27A:
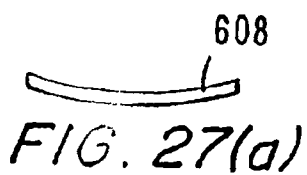
Figure 27:
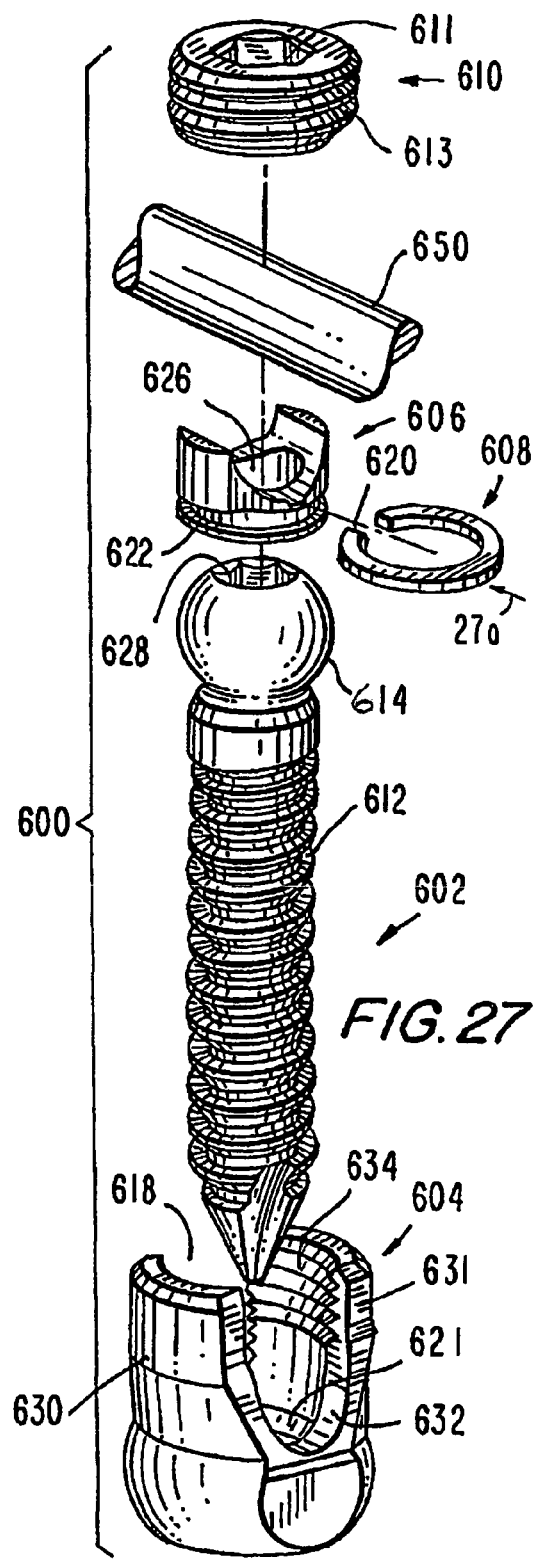
FIG. 27 is an exploded perspective view of the fastener of FIG. 26.

FIGS. 26-27 illustrate a fastener 600 that is particularly applicable in a procedures involving fixation. The fastener 600 is described in greater detail in U.S. patent application Ser. No. 10/075,668, filed Feb. 13, 2002 and application Ser. No. 10/087,489, filed Mar. 1, 2002, which are incorporated by reference in their entirety herein. Fastener 600 includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole 92 in the vertebrae, as will be described below. The substantially spherical joint portion 614 is received in a substantially annular, part spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604, until the joint portion 614 engages the annular recess 616. The screw portion 602 is retained in the housing 604 by the spacer member 606 and biasing member 608. The biasing member 608 provides a biasing force to drive the spacer member 606 in frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 is selected such that biasing force prevents unrestricted movement of the housing 604 relative to the screw portion 602. However, the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27($a$) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 which is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright member 630 and 631. Elongated member 650 to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

The fastener 600 is inserted into the expandable conduit 20 and guided to the prepared hole 92 in the vertebrae as a further stage of the procedure. The fastener 600 must be simultaneously supported and rotated in order to be secured in hole 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

The distal tool portion 666, as illustrated in greater detail in FIG. 29 includes a substantially hexagonal outer periphery which is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel/groove is provided in the tip portion 666 for receiving the spring member 672. The channel/groove includes a medial longitudinal notch portion 676, a proximal, angled channel portion 678, and a distal substantially transverse channel portion 680. The spring member 672 is preferably manufactured from stainless steel and has a medial portion 682 that is partially received in the longitudinal notch portion 676, an angled proximal portion 684 which is fixedly received in the angled charnel portion 678, and a transverse distal portion 686 which is slidably received in the transverse channel 680. The medial portion 682 of the spring member 672 is partially exposed from the distal tip portion 666 and normally biased in a transverse outward direction with respect to the longitudinal axis (indicated by arrow E), in order to supply bearing force against the wall of the recess 628. Alternatively the distal tip portion of the screw driver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666.

The insertion of the fastener 600 into the prepared hole 92 may be achieved by insertion of screwdriver 660 into conduit 20 (indicated by arrow G). This procedure may be visualized by the use of the endoscope 500 in conjunction with fluoroscopy. The screw portion 602 is threaded into the prepared hole 92 by the endoscopic screwdriver 660 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the expandable conduit 20. An alternative method may use a guidewire, which is fixed in the hole 92, and a cannulated screw which has an internal lumen (as is known in the art) and is guided over the guidewire into the hole 92. The screwdriver would be cannulated as well to fit over the guidewire.

For a two-level fixation, it may be necessary to prepare several holes and attach several fasteners 600. Typically, the expandable conduit 20 will be sized in order to provide simultaneous access to all vertebrae in which the surgical procedure is being performed. In some cases, however, additional enlargement or repositioning of the distal portion of the expandable conduit may be required in order to have sufficient access to the outer vertebrae, e.g., the L4 and S1 vertebrae. In the illustrated embodiment, the expander apparatus 200 may be repeatedly inserted into the expandable conduit 20 and expanded in order to further open or position the skirt portion 24. In one procedure, additional fasteners are inserted in the L4 and S1 vertebrae in a similar fashion as the fastener 600 inserted in to the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In a further stage of the procedure, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step, described below. Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. As is known in the art, pivoting the movable handle 714 towards stationary handle 714 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

A subsequent stage in the process is the insertion of the elongated member 650 into the expandable conduit. The elongated member 650 is manufactured from a biocompatible material and must be sufficiently strong to maintain the positioning of the vertebrae, or other body structures. In the exemplary embodiment, the elongated members 650 are manufactured from Titanium 6/4 or titanium alloy. Alternatively, the elongated member 650 may be manufactured from stainless steel or other suitable material. The radii and length of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

The elongated member 650 is subsequently fixed to each of the fasteners 600, and more particularly, to the housings 604 of each fastener 600. The grasper apparatus 700, described above, is also particularly useful for inserting the elongated member 650 into the expandable conduit 20 and positioning it with respect to each housing 604. As illustrated in FIG. 30, the jaws 708a and 708b of the grasper apparatus 700 each has a curved contact portion 722a and 722b for contacting and holding the outer surface of the elongated member 650.

As illustrated in FIG. 31, the grasper apparatus 700 may be used to insert the elongated member 650 into the operative space 90 defined at least partially by the skirt portion 24 of the expandable conduit 20. The cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housing 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion 802 extends transverse to the longitudinal axis 810, which allows the physician to adjust the guide apparatus 800 without interfering with the operation of the screwdriver 660.

The distal portion 806 of the apparatus includes several semicircular cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location.

As illustrated in FIG. 34, the guide apparatus 800 is used in cooperation with the endoscopic screwdriver 660 to attach the cap screw 610. The distal end of the body portion 804 includes a pair of elongated openings 816, which permit the physician to endoscopically view the cap screw 610 retained at the distal tip 666 of the endoscopic screw driver 660.

The guide apparatus 800 and the endoscopic screwdriver 660 may cooperate as follows. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
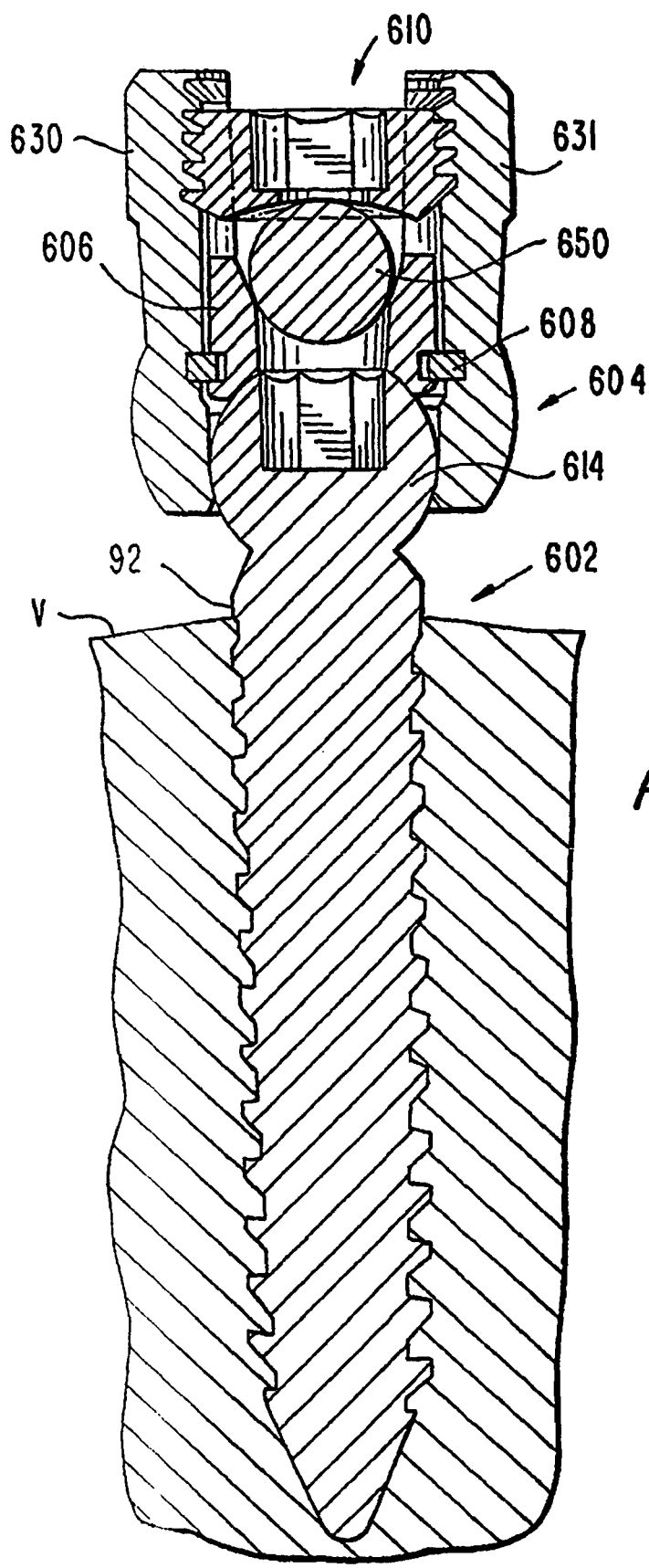
FIG. 35 is an enlarged sectional similar to FIG. 34, illustrating one embodiment of a stage of one embodiment of a method for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is consequently fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of the compressor-distractor instrument 900 is illustrated in FIG. 36. (Further details of the compressor-distractor apparatus is described in co-pending U.S. application Ser. No. 10/178,875, filed Jun. 24, 2002, entitled "Surgical Instrument for Moving Vertebrae," which is incorporated by reference in its entirety herein.) The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 is a jaw portion which is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis.

As illustrated in FIG. 36, the spacer member 906 can be opened with respect to the driver portion 904 to space the vertebrae further apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 610 of spacer member 606 engages housing 604b of fastener 600b and moves fastener 600b towards fastener 600a. When the spacing of the vertebrae is acceptable to the physician, the cap screw 610a is tightened by the driver member 904, thereby fixing the relationship of the housing 604a with respect to elongated member 650, and thereby fixing the position of the vertebrae, or other bone structures, with respect to one another.

Once the elongated member 650 is fixed with respect to the fasteners 600, the procedure is substantially complete. The surgical instrumentation, such as the endoscope 500 is withdrawn from the surgical site. The expandable conduit 20 is also withdrawn from the site. The muscle and fascia typically close as the expandable conduit 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Surgical Procedures that may be Performed with the Systems Described Herein As discussed above, the systems disclosed herein provide access to a surgical location at or near the spine of a patient to enable procedures to be performed on the spine. These procedures can be applied to one or more vertebral levels. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described above.

A. Procedures Involving Anterior Lumbar Interbody Fusion

The access devices and systems described herein are amenable to a variety of procedures that may be combined with an anterior lumbar interbody fusion (referred to herein as an "ALIF").

In one embodiment of a first method, three adjacent vertebrae, such as the L4, the L5, and the S1 vertebrae of the spine, are treated by first performing an ALIF procedure. Such a procedure may be performed in a convention manner. The ALIF involves exposing a portion of the spine, in particular the vertebrae and discs located in the interbody spaces, i.e., the spaces between adjacent vertebrae. Any suitable technique for exposing the interbody spaces may be employed, e.g., an open, mini-open, or minimally invasive procedure. In one embodiment, the interbody spaces between the L4, L5, and S1 vertebrae are exposed to the surgeon. Once exposed, the surgeon may prepare the interbody space, if needed, in any suitable manner. For example, some or all of the disc may be removed from the interbody space and the height of the interbody space may be increased or decreased. The interbody space between the L4 and the L5 vertebrae may be exposed separately from the interbody space between the L5 and S1 vertebrae or they may be generally simultaneously exposed and prepared.

After the interbody space has been exposed and prepared, a suitable fusion procedure may be performed. For example, in one example fusion procedure, one or more fusion devices may be placed in the interbody space. Any suitable fusion device may be used, e.g., a fusion cage, a femoral ring, or another suitable implant. Various embodiments of implants and techniques and tools for the insertion of implants are described in U.S. application Ser. No. 10/280,489, filed Oct. 25, 2002, which has been published as Publication No. 2003/0073998 on Apr. 17, 2003, which is hereby incorporated by reference herein in its entirety. In one variation, one or more fusion cages may be placed in an interbody space, e.g., between the L4 and L5 vertebrae, between the L5 and S1 vertebrae, or between the L4 and L5 vertebrae and between the L5 and S1 vertebrae. In another variation, one or more femoral rings may be substituted for one or more of the fusion cages and placed between the L4 and L5 vertebrae and/or between the L5 and S1 vertebrae. In another variation, one or more fusion devices are combined with a bone growth substance, e.g., bone chips, to enhance bone growth in the interbody space(s).

After anterior placement of the fusion device, an access device is inserted into the patient to provide access to a spinal location, as described above. A variety of anatomical approaches may be used to provide access to a spinal location using the expandable conduit 20. The access device preferably is inserted generally posteriorly. As used herein the phrase "generally posteriorly" used in its ordinary sense and is a broad term that refers to a variety of surgical approaches to the spine that may be provided from the posterior side, i.e., the back, of the patient, and includes, but is not limited to, posterior, postero-lateral, and transforaminal approaches. Any of the access devices described or incorporated herein, such as the expandable conduit 20, could be used.

The distal end of the access device may be placed at the desired surgical location, e.g., adjacent the spine of the patient with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device in other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the adjacent vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae above and below the first vertebra.

When it is desired to treat the L4, L5, and S1 vertebrae, the access device may be inserted over the L5 vertebrae and then expanded to provide increased access to the L4 and S1 vertebrae. In one embodiment, the access device can be expanded to an oblong shaped configuration wherein the access device provides a first dimension of about 63 mm, and a second dimension perpendicular to the first dimension of about 24 mm. In another embodiment, the access device can be expanded to provide a first dimension of about 63 mm, and a second dimension perpendicular to the first dimension of about 27 mm. These dimensions provide a surgical space that is large enough to provide access to at least three adjacent vertebrae without exposing excessive amounts of adjacent tissue that is not required to be exposed for the procedures being performed. Other dimensions and configurations are possible that would provide the needed access for procedures involving three adjacent vertebrae.

When the access device is in the second configuration, fixation of the three vertebrae may be performed. As discussed above, fixation is a procedure that involves providing a generally rigid connection between at least two vertebrae. Any of the fixation procedures discussed above could be used in this method, as could other fixation procedures. One fixation procedure that could be used is discussed above in connection with FIG. 36 wherein the fasteners 600a, 600b, and 600c are advanced through the expandable conduit 20 to three adjacent vertebrae and are attached to the vertebrae. The three fasteners 600a, 600b, and 600c are interconnected by the elongated member 650. The three fasteners 600a, 600b, and 600c and the elongate member 650 comprise a first fixation assembly. A second fixation assembly may be applied to the patient on the opposite side of the spine, i.e., about the same location on the opposite side of the medial line of the spine. Other fixation procedures could be applied, e.g., including two fasteners that coupled to the L4 and the S1 vertebrae and an elongate member interconnecting these vertebrae.

One variation of the first method provides one level of fixation on the anterior side of the patient, e.g., when the fusion device is placed in the interbody space. For example, fixation of the L5 and S1 vertebrae could be provided on the anterior side of the spine, in addition to the other procedures set forth above (e.g., a two level postero-lateral fixation). Also, fixation of the L4 and L5 vertebrae could be provided on the anterior side of the spine, in addition to the other procedures set forth above (e.g., a two level postero-lateral fixation).

In a second method, substantially the same steps as set forth above in connection with the first method would be performed. In addition, after the access device is inserted, a decompression procedure is performed through the access device. A decompression procedure is one where unwanted bone is removed from one or more vertebrae. Unwanted bone can include stenotic bone growth, which can cause impingement on the existing nerve roots or spinal cord. Decompression procedures that may be performed include laminectomy, which is the removal of a portion of a lamina(e), and facetectomy, which is the removal of a portion of one or more facets. In one variation of this method, decompression includes both a facetectomy and a laminectomy. Any suitable tool may be used to perform decompression. One tool that is particularly useful is a kerrison.

In a third method, substantially the same steps as set forth above in connection with the first method would be performed. That is, an ALIF procedure is performed in combination with a fixation procedure. In addition, a fusion procedure may be performed through the access device which may have been placed generally posteriorly, e.g., postero-laterally, tranforaminally or posteriorly, whereby bone growth is promoted between the vertebrae and the fixation assembly, including at least one of the fasteners 600a, 600b, 600c and/or the elongate element 650. This procedures is also referred to herein as an "external fusion" procedure.

One example of an external fusion procedure that may be performed involves placement of a substance through the access device intended to encourage bone growth in and around the fixation assembly. Thus, fusion may be enhanced by placing a bone growth substance adjacent any of the fasteners 600a, 600b, 600c and/or the elongate member 650. The bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance can cause bone to bridge across from the vertebra(e) to one or more components of the fixation assembly.

In a fourth method, substantially the same steps as set forth above in connection with the second method would be performed. That is, an ALIF procedure is performed anteriorly, and a decompression procedure and a fixation procedure are performed through the access device which may be placed generally posteriorly, e.g., postero-laterally, tranforaminally, or posteriorly. In addition, bone growth substance is placed in and around a fixation assembly through the access device, as discussed above in connection with the third method. The bone growth substance encourages bone to bridge across from the vertebrae to the fixation assembly.

In a fifth method, an ALIF procedure is performed, as discussed above in connection with the second method. After one or more fusion devices is placed in the interbody space, access is provided by way of the access device, as discussed above, from any suitable anatomical approach, e.g., a generally posterior approach. Preferably, a postero-lateral approach is provided. After access has been provided, a bone growth substance, such as those discussed above in connection with the third method, is delivered through the access device. The bone growth substance is placed adjacent an interbody space, e.g., the space between the L4 and the L5 vertebrae and/or between the L5 and the S1 vertebrae. The bone growth substance encourages fusion of the adjacent vertebrae, e.g., L4 to L5 and/or L5 to S1, by stimulating or enhancing the growth of bone between adjacent vertebrae, as discussed above.

In a sixth method, substantially the same steps described in connection with the first method are performed, except that the fixation procedure is optional. In one variation of the sixth method, the fixation procedure is not performed. However, after the access device is inserted, a bone growth substance is placed in and around one or more interbody spaces through the access device. Where the sixth method involves a two level procedure, the bone growth substance can be placed adjacent the interbody space between the L4 and the L5 vertebra and/or between the L5 and the S1 vertebra. Thus, bone growth may occur in the interbody space and adjacent the interbody space between the vertebrae.

The foregoing discussion illustrates that an ALEF procedure can be combined with a variety of procedures that can be performed through an access device disclosed herein. In addition, though not expressly set forth herein, any combination of the procedures discussed above, and any other suitable known procedure, may also be combined and performed through the access devices described herein, as should be understood by one skilled in the art.

B. Spine Procedures Providing Minimally Invasive Lumbar Interbody Fusion

Another category of procedures that may be performed with the access devices and systems described above involves a minimally invasive lumbar interbody fusion (referred to herein as a "MILIF"). MILIF procedures are particularly advantageous because they permit the surgeon to perform a wide variety of therapeutic procedures without requiring fusion by way of an anterior approach, as is required in an ALIF. This provides a first advantage of allowing the surgeon to perform all procedures from the same side of the patient and also possibly from the same approach. Also, the access devices and systems disclosed herein provide the further advantage of enabling two level procedures, and many other related procedures, to be performed by way of a single percutaneous access. These and other advantages are explained more fully below.

In a first MILIF method, a two level postero-lateral fixation of the spine involving three adjacent vertebrae, such as the L4, L5, and S1 vertebrae, is provided. Analogous one level procedures and two level procedures involving any other three vertebrae also may be provided. In addition, the access devices and systems described herein could be used or modified to accommodate other multi-level procedures, such as a three level procedure. The surgeon inserts an access device such as described herein to a surgical location near the spine. As discussed above, the access devices are capable of a wide variety of anatomical approaches. In this procedure, a postero-lateral approach is preferred. Once the access device is inserted to a location adjacent the spine, as discussed above, it may be configured, e.g., expanded, as discussed above, to a configuration wherein sufficient access is provided to the surgical location.

Any suitable fusion process may then be performed. For example, an implant may advanced through the access device into the interbody space in order to maintain disc height and allow bone growth therein, e.g. as in a fusion procedure. In order to ease insertion of the implant, it may be beneficial to prepare the interbody space. Interbody space preparation may involve removal of tissue or adjusting the height of the interbody space through the access device, such as in a distraction procedure. Once the interbody space is prepared, a suitable implant may be advanced through the access device into the interbody space, taking care to protect surrounding tissues. Various embodiments of implants and techniques and tools for their insertion are described in U.S. application Ser. No. 10/280,489, incorporated by reference hereinabove. In general, the implant preferably is an allograft strut that is configured to maintain disc height and allow bone growth in the interbody space.

In addition to providing a suitable fusion, the first method provides fixation of the vertebrae. The fixation procedure may take any suitable form, e.g., any of the fixation procedures similar to those disclosed above. In particular, when the access device is in the expanded or enlarged configuration, fixation of the three adjacent vertebrae may be performed. One fixation procedure that could be used is discussed above in connection with FIG. 36 wherein the fasteners 600a, 600b, and 600c are advanced through the expandable conduit 20 to three adjacent vertebrae and are attached to the vertebrae. The three fasteners 600a, 600b, and 600c are interconnected by way of the elongated member 650. As discussed above, a second fixation assembly may be applied to the patient on the opposite side of the spine, e.g., about the same location on the opposite side of the medial line of the spine.

In a second MELIF method, substantially the same procedures set forth above in connection with the first MILIF method are performed. In addition, a suitable decompression procedure may be performed, as needed. As discussed above, decompression involves removal of unwanted bone by way of a suitable decompression technique that may be performed through the access device. In one embodiment, decompression is performed through the access device after the access device has been expanded. As discussed above, suitable decompression techniques include a laminectomy, a facetectomy, or any other similar procedure. Decompression for the L4, the L5, and/or the S1 vertebrae may be needed and can be performed through the access devices described herein without requiring the access device to be moved from one position to another.

In a third MILIF method, substantially the same procedures set forth above in connection with the first MILIF method are performed. In addition, a further fusion procedure, e.g., a fusion procedure external to the interbody space, is provided. The external fusion procedure is performed adjacent to the interbody space wherein bone growth may be promoted in the proximity of the fixation assembly, e.g., above the postero-lateral boney elements of the spine, such as the facet joints and the transverse processes. In one embodiment, when the fixation assembly comprising the fasteners 600a, 600b, 600c and/or the elongate element 650 has been applied to three adjacent vertebrae, a substance is applied through the access device to one or more components of the fixation assembly to maintain or enhance the formation and/or growth of bone in the proximity of the fixation assembly. For example, a bone growth substance may be placed adjacent any of the fasteners 600a, 600b, 600c and/or the elongate member 650. Bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance advantageously causes bone to grow between the vertebrae and the fixation assembly to form a bridge therebetween.

A fourth MILIF method involves substantially the same procedures performed in connection with the third MILIF method. In particular, one or more implants are positioned in the interbody spaces through an access device, a fixation procedure is performed through the access device, and a further fusion procedure is performed wherein bone growth substance is positioned adjacent the interbody space through the access device. In addition, a decompression procedure is performed through the access device that may include a facetectomy and/or a laminectomy.

A fifth MILIF method involves substantially the same procedures performed in connection with the first MILIF method, except that the fixation is optional. In one embodiment, the fixation is not performed. In addition, a further fusion procedure is performed through the access device wherein bone growth substance is positioned adjacent the interbody space, as discussed above.

A sixth MILIF method is substantially the same as the fifth MILIF method, except that a further fusion procedure is performed through the access device. In particular, an implant is positioned in the interbody space through an access device, a decompression procedure is performed through the access device, and a further fusion procedure is performed whereby bone growth substance is placed adjacent the interbody space through the access device. As discussed above, the decompression procedure may include a facetectomy, a laminectomy, and any other suitable procedure. As with any of the methods described herein, the procedures that make up the sixth MILIF method may be performed in any suitable order. Preferably the decompression procedure is performed before the external fusion procedure.

The foregoing discussion illustrates that a MILIF procedure can include a variety of procedures that can be performed through an access device described herein. In addition, though not expressly set forth herein, any combination of the procedures discussed above, and any other suitable known procedures, may also be combined, as should be understood by one skilled in the art.

C. Other Multi-level Procedures

While the foregoing procedures have involved interbody fusion, the access devices and systems described herein can be employed in a variety of single level and multi-level procedures (e.g., more than two levels) that do not involve an interbody fusion. For example, a discectomy can be performed through the access devices described herein without implanting an interbody fusion device thereafter, e.g., to remove a hemeation. In another embodiment, a discectomy can be performed in more than one interbody space without inserting an interbody fusion device into each interbody space, e.g., to remove multiple herneations. In another embodiment, a single or multi-level decompression procedure can be performed to remove unwanted bone growth.

It will be understood that the foregoing is only illustrative of the principles of the invention, and that various modifications, alterations, and combinations can be made by those skilled in the art without departing from the scope and spirit of the invention.

What is claimed is:

1. A method of treating the spine of a patient, comprising:
    inserting an access device through an incision in the skin of the patient generally posteriorly until a distal portion of the access device is located adjacent the spine of the patient, said access device being inserted in a first configuration having a first cross-sectional area at the distal portion thereof;
    actuating said access device to a second configuration having an enlarged cross-sectional area at said distal portion thereof that spans at least a portion of a first vertebra, at least a portion of a second vertebra, and at least a portion of a third vertebra;
    placing a fusion device through the access device and in at least one of a first interbody space between the first and second vertebrae and a second interbody space between the second and third vertebrae;
    performing a two level fixation procedure spanning the first and second interbody spaces through the access device by inserting at least one fastener into each of the first, second, and third vertebrae and attaching an elongated member to the fasteners, wherein the fastener includes a screw and a U-shaped housing adapted to receive a joint region of the screw and the elongated member, wherein the housing and joint region are configured to allow movement of the housing relative to the screw to achieve a desired orientation of the elongated member with respect to the housing;
    advancing a decompression tool through the access device; and
    removing a portion of bone from one of the first vertebrae, the second vertebrae, and the third vertebrae through the access device;
    wherein the steps of placing the fusion device in an interbody space, inserting fasteners into first, second, and third vertebrae, attaching an elongated member to the fasteners, advancing a decompression tool, and removing a portion of bone from a vertebrae are all performed through the same access device with the access device inserted in the same incision.

2. The method of claim 1, wherein the portion of bone removed comprises a portion of a facet.

3. The method of claim 1, wherein the portion of bone removed comprises a portion of a lamina.

4. The method of claim 1, further comprising placing a bone growth substance through the access device and adjacent at least one of the first interbody space and the second interbody space to enhance bone growth therebetween.

5. A method of treating a spine of a patient, comprising:
    inserting an access device through an incision in the skin of the patient generally posteriorly until a distal portion of the access device is located adjacent the spine of the patient, said access device being inserted in a first configuration having a first cross-sectional area at the distal portion thereof;
    actuating said access device to a second configuration having an enlarged cross-sectional area at said distal portion thereof that spans at least a portion of each of a first vertebra, a second vertebra, and a third vertebra;
    placing a fusion device through the access device and in at least one of a first interbody space between the first and second vertebrae and a second interbody space between the second and third vertebrae;
    inserting two or more fasteners through the access device and into at least two of said first, second, and third vertebrae, each fastener including a screw and a housing, the housing having a pair of upright members forming grooves therebetween shaped to receive an elongated member;
    inserting the elongated member through the access device and into the housing grooves of each fastener;
    moving each housing relative to its associated screw to achieve a desired orientation; and
    placing a bone growth substance through the access device and adjacent at least one of the first interbody space and the second interbody space to enhance bone growth therebetween;
    wherein the steps of placing a fusion device in an interbody space, inserting two or more fasteners into two vertebrae, inserting an elongated member into housing grooves of each fastener, moving the housings relative to the screws, and placing a bone growth substance adjacent an interbody space are all performed through the same access device with the access device inserted in the same incision.

6. The method of claim 5, further comprising:
    advancing a decompression tool through the access device; and
    removing a portion of bone from one of the first vertebrae, the second vertebrae, and the third vertebrae through the access device.

7. The method of claim 6, wherein the portion of bone removed comprises a portion of a facet.

8. The method of claim 6, wherein the portion of bone removed comprises a portion of a lamina.

9. A method of treating the spine of a patient, comprising:
inserting an access device through an incision in the skin of the patient generally posteriorly until a distal portion of the access device is located adjacent the spine of the patient, said access device being inserted in a first configuration having a first cross-sectional area at the distal portion thereof;
actuating said access device to a second configuration having an enlarged cross-sectional area at said distal portion thereof that spans at least a portion of a first vertebra, at least a portion of a second vertebra, and at least a portion of a third vertebra;
placing a fusion device through the access device and in at least one of a first interbody space between the first and second vertebrae and a second interbody space between the second and third vertebrae;
performing a two level fixation procedure spanning the first and second interbody spaces though the access device, said two level fixation procedure including:
   inserting three or more fasteners through the access device and into the first, second, and third vertebrae, each fastener including a screw and a U-shaped housing configured to receive an elongated member;
   inserting the elongated member through the access device and into the housings;
   moving each housing relative to its associated screw to achieve a desired orientation;
advancing a decompression tool through the access device; and
removing a portion of a facet from one of the first vertebrae, the second vertebrae, and the third vertebrae through the access device;
wherein the steps of placing a fusion device in an interbody space, inserting three or more fasteners into three vertebrae, inserting the elongated member into the housings, moving the housings, advancing a decompression tool, and removing a portion of a facet from a vertebrae are all performed through the same access device with the access device inserted in the same incision.

10. A method of treating a spine of a patient, comprising:
inserting an access device through an incision in the skin of the patient generally posteriorly until a distal portion of the access device is located adjacent the spine of the patient, said access device being inserted in a first configuration having a first cross-sectional area at the distal portion thereof;
actuating said access device to a second configuration having an enlarged cross-sectional area at said distal portion thereof that spans at least a portion of each of a first vertebra, a second vertebra, and a third vertebra;
inserting two or more fasteners through the access device and into at least two of said first, second, and third vertebrae, each fastener including a screw and a U-shaped housing configured to receive an elongated member;
inserting the elongated member through the access device and into the housings;
temporarily securing the elongated member to the housings;
moving each housing relative to its associated screw to achieve a desired orientation;
placing a fusion device through the access device and in at least one of a first interbody space between the first and second vertebrae and a second interbody space between the second and third vertebrae;
placing a bone growth substance through the access device and adjacent at least one of the first interbody space and the second interbody space to enhance bone growth therebetween;
advancing a decompression tool through the access device;
removing a portion of a facet from one of the first vertebrae, the second vertebrae, and the third vertebrae through the access device; and
permanently securing the elongated member to the housings;
wherein the steps of inserting fasteners into vertebrae, inserting the elongated member into the housings, temporarily securing the elongated member to the housings, moving the housings, placing a fusion device in an interbody space, placing a bone growth substance adjacent an interbody space, advancing a decompression tool, removing a portion of a facet from a vertebrae, and permanently securing the elongated member to the housings are all performed through the same access device with the access device inserted in the same incision.

* * * * *

UNITED STATES PATENT AND TRADEMARK OFFICE
CERTIFICATE OF CORRECTION

| | | |
|---|---|---|
| PATENT NO. | : 7,985,247 B2 | Page 1 of 1 |
| APPLICATION NO. | : 10/658736 | |
| DATED | : July 26, 2011 | |
| INVENTOR(S) | : Alan Shluzas et al. | |

It is certified that error appears in the above-identified patent and that said Letters Patent is hereby corrected as shown below:

Column 17
Line 36, delete "charnel", and insert therefor -- channel --.

Column 20
Line 49, delete "incorporated by reference in its entirety", and insert therfor -- incorporated by reference in its entirety --.

Column 24
Line 64, delete "ALEF", and insert therefor -- ALIF --.

Column 26
Line 3, delete "MELIF", and insert therefor -- MILIF --.

Column 27
Line 27, delete "hemeation", and insert therefor -- herneation --.

Signed and Sealed this
Thirtieth Day of August, 2011

David J. Kappos
*Director of the United States Patent and Trademark Office*